(12) United States Patent
Panescu et al.

(10) Patent No.: US 10,413,212 B2
(45) Date of Patent: *Sep. 17, 2019

(54) METHODS AND SYSTEMS FOR ENHANCED MAPPING OF TISSUE

(71) Applicant: Epix Therapeutics, Inc., Santa Clara, CA (US)

(72) Inventors: Dorin Panescu, San Jose, CA (US); Josef Vincent Koblish, Sunnyvale, CA (US); Jessi E. Johnson, Sunnyvale, CA (US)

(73) Assignee: Epix Therapeutics, Inc., Menlo Park, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 15/369,779

(22) Filed: Dec. 5, 2016

(65) Prior Publication Data

US 2017/0079545 A1 Mar. 23, 2017

Related U.S. Application Data

(63) Continuation of application No. 15/179,891, filed on Jun. 10, 2016, now Pat. No. 9,510,905, which is a
(Continued)

(51) Int. Cl.
*A61B 18/12* (2006.01)
*A61B 5/053* (2006.01)
(Continued)

(52) U.S. Cl.
CPC .......... *A61B 5/0538* (2013.01); *A61B 5/6858* (2013.01); *A61B 17/320068* (2013.01);
(Continued)

(58) Field of Classification Search
CPC ........ A61B 17/320068; A61B 18/0218; A61B 18/1492; A61B 18/1815; A61B 18/24;
(Continued)

(56) References Cited

U.S. PATENT DOCUMENTS 4,190,053 A 2/1980 Sterzer
4,197,860 A 4/1980 Sterzer
(Continued)

FOREIGN PATENT DOCUMENTS

EP 0746372 5/2003
EP 1008327 10/2008
(Continued)

OTHER PUBLICATIONS

Anter et al, "High-Resolution Mapping of Scar-Related Atrial Arrhythmias Using Smaller Electrodes with Closer Interelectrode Spacing," Circ. Arrhythm. Electrophysiol. 8(3):537-45 (2015).
(Continued)

*Primary Examiner* — Daniel W Fowler
(74) *Attorney, Agent, or Firm* — Christopher & Weisberg, P.A.

(57) ABSTRACT

According to some embodiments, methods and systems of enhancing a map of a targeted anatomical region comprise receiving mapping data from a plurality of mapping electrodes, receiving high-resolution mapping data from a high-resolution roving electrode configured to be moved to locations between the plurality of mapping electrodes, wherein the mapping system is configured to supplement, enhance or refine a map of the targeted anatomical region or to directly create a high-resolution three-dimensional map using the processor receiving the data obtained from the plurality of mapping electrodes and from the high-resolution roving electrode.

14 Claims, 14 Drawing Sheets

Related U.S. Application Data continuation of application No. PCT/US2015/061353, filed on Nov. 18, 2015.

(60) Provisional application No. 62/159,898, filed on May 11, 2015, provisional application No. 62/081,710, filed on Nov. 19, 2014.

(51) Int. Cl.

| | | |
|---|---|---|
| *A61B 18/14* | (2006.01) | |
| *A61B 5/00* | (2006.01) | |
| *A61B 17/32* | (2006.01) | |
| *A61B 18/02* | (2006.01) | |
| *A61B 18/18* | (2006.01) | |
| *A61B 18/24* | (2006.01) | |
| A61B 18/00 | (2006.01) | |
| A61B 5/042 | (2006.01) | |
| A61B 17/00 | (2006.01) | |

(52) U.S. Cl.
CPC ...... *A61B 18/0218* (2013.01); *A61B 18/1492* (2013.01); *A61B 18/1815* (2013.01); *A61B 18/24* (2013.01); A61B 5/0422 (2013.01); A61B 2017/00026 (2013.01); A61B 2017/00044 (2013.01); A61B 2018/0016 (2013.01); A61B 2018/0066 (2013.01); A61B 2018/00083 (2013.01); A61B 2018/00267 (2013.01); A61B 2018/00351 (2013.01); A61B 2018/00357 (2013.01); A61B 2018/00577 (2013.01); A61B 2018/00642 (2013.01); A61B 2018/00732 (2013.01); A61B 2018/00791 (2013.01); A61B 2018/00839 (2013.01); A61B 2018/00875 (2013.01); A61B 2018/1467 (2013.01); A61B 2218/002 (2013.01)

(58) Field of Classification Search
CPC ........... A61B 2017/00026; A61B 2017/00044; A61B 2018/00083; A61B 2018/0016; A61B 2018/00267; A61B 5/0422; A61B 5/0538; A61B 5/6858
See application file for complete search history.

(56) References Cited

U.S. PATENT DOCUMENTS

| | | |
|---|---|---|
| 4,346,716 A | 8/1982 | Carr |
| 4,557,272 A | 12/1985 | Carr |
| 4,614,514 A | 9/1986 | Carr et al. |
| 4,632,127 A | 12/1986 | Sterzer |
| 4,647,281 A | 3/1987 | Carr |
| 4,686,498 A | 8/1987 | Carr et al. |
| 4,715,727 A | 12/1987 | Carr |
| 4,727,874 A | 3/1988 | Bowers et al. |
| 4,774,961 A | 10/1988 | Carr |
| 4,815,479 A | 3/1989 | Carr |
| 4,922,912 A | 5/1990 | Watanabe |
| 4,945,912 A | 8/1990 | Langberg |
| 4,955,382 A | 9/1990 | Franz et al. |
| 4,979,510 A | 12/1990 | Franz et al. |
| 5,073,167 A | 12/1991 | Carr et al. |
| RE33,791 E | 1/1992 | Carr |
| 5,105,808 A | 4/1992 | Neuwirth et al. |
| 5,149,198 A | 9/1992 | Sterzer |
| 5,176,146 A | 1/1993 | Chive et al. |
| 5,198,776 A | 3/1993 | Carr |
| 5,230,349 A | 7/1993 | Landberg |
| 5,282,840 A | 2/1994 | Hudrlik |
| 5,334,141 A | 8/1994 | Carr et al. |
| 5,334,193 A | 8/1994 | Nardella |
| 5,344,435 A | 9/1994 | Turner et al. |
| 5,354,325 A | 10/1994 | Chive et al. |
| 5,364,336 A | 11/1994 | Carr |
| 5,370,676 A | 12/1994 | Sozanski et al. |
| 5,383,874 A | 1/1995 | Jackson et al. |
| 5,385,146 A | 1/1995 | Goldreyer |
| 5,398,683 A | 3/1995 | Edwards et al. |
| 5,456,682 A | 10/1995 | Edwards et al. |
| 5,462,521 A | 10/1995 | Brucker et al. |
| 5,485,849 A | 1/1996 | Panescu et al. |
| 5,487,391 A | 1/1996 | Panescu |
| 5,494,042 A | 2/1996 | Panescu et al. |
| 5,514,130 A | 5/1996 | Baker |
| 5,522,815 A | 6/1996 | Durgin, Jr. et al. |
| 5,531,662 A | 7/1996 | Carr |
| 5,540,655 A | 7/1996 | Edwards et al. |
| 5,546,940 A | 8/1996 | Panescu et al. |
| 5,549,639 A | 8/1996 | Ross |
| 5,562,619 A | 10/1996 | Mirarchi et al. |
| 5,577,509 A | 11/1996 | Panescu et al. |
| 5,582,589 A | 12/1996 | Edwards et al. |
| 5,582,609 A | 12/1996 | Swanson et al. |
| 5,584,830 A | 12/1996 | Ladd et al. |
| 5,591,125 A | 1/1997 | Edwards et al. |
| 5,595,183 A | 1/1997 | Swanson et al. |
| 5,598,848 A | 2/1997 | Swanson et al. |
| 5,599,295 A | 2/1997 | Rosen et al. |
| 5,601,088 A | 2/1997 | Swanson et al. |
| 5,605,157 A | 2/1997 | Panescu et al. |
| 5,609,157 A | 3/1997 | Panescu et al. |
| 5,616,268 A | 4/1997 | Carr |
| 5,624,392 A | 4/1997 | Saab |
| 5,630,425 A | 5/1997 | Panescu et al. |
| 5,643,197 A | 7/1997 | Brucker et al. |
| 5,647,870 A | 7/1997 | Kordis et al. |
| 5,651,780 A | 7/1997 | Jackson et al. |
| 5,656,030 A | 8/1997 | Hunjan et al. |
| 5,658,278 A | 8/1997 | Imran et al. |
| 5,662,110 A | 9/1997 | Carr |
| 5,667,488 A | 9/1997 | Lundquist et al. |
| 5,672,174 A | 9/1997 | Gough et al. |
| 5,673,704 A | 10/1997 | Marchlinski et al. |
| 5,674,191 A | 10/1997 | Edwards et al. |
| 5,683,381 A | 11/1997 | Carr et al. |
| 5,683,382 A | 11/1997 | Lenihan et al. |
| 5,683,384 A | 11/1997 | Gough et al. |
| 5,685,839 A | 11/1997 | Edwards et al. |
| 5,685,878 A | 11/1997 | Falwell et al. |
| 5,688,050 A | 11/1997 | Sterzer et al. |
| 5,688,266 A | 11/1997 | Edwards et al. |
| 5,688,267 A | 11/1997 | Panescu et al. |
| 5,690,614 A | 11/1997 | Carr et al. |
| 5,702,386 A | 12/1997 | Stern et al. |
| 5,707,369 A | 1/1998 | Vaitekunas et al. |
| 5,711,305 A | 1/1998 | Swanson et al. |
| 5,712,047 A | 1/1998 | Aso et al. |
| 5,715,832 A | 2/1998 | Koblish et al. |
| 5,718,701 A | 2/1998 | Shai et al. |
| 5,722,402 A | 3/1998 | Swanson et al. |
| 5,722,403 A | 3/1998 | McGee et al. |
| 5,722,416 A | 3/1998 | Swanson et al. |
| 5,732,698 A | 3/1998 | Swanson et al. |
| 5,735,846 A | 4/1998 | Panescu et al. |
| 5,735,847 A | 4/1998 | Gough et al. |
| 5,740,808 A | 4/1998 | Panescu et al. |
| 5,743,903 A | 4/1998 | Stern et al. |
| 5,752,518 A | 5/1998 | McGee et al. |
| 5,755,715 A | 5/1998 | Stern et al. |
| 5,762,786 A | 6/1998 | Oelbermann |
| 5,769,846 A | 6/1998 | Edwards et al. |
| 5,769,847 A | 6/1998 | Panescu et al. |
| 5,779,635 A | 7/1998 | Carr |
| 5,779,646 A | 7/1998 | Koblish et al. |
| 5,782,827 A | 7/1998 | Gough et al. |
| 5,782,828 A | 7/1998 | Chen et al. |
| 5,782,897 A | 7/1998 | Carr |
| 5,792,064 A | 8/1998 | Panescu et al. |
| 5,792,140 A | 8/1998 | Tu et al. |
| 5,795,303 A | 8/1998 | Swanson et al. |
| 5,797,903 A | 8/1998 | Swanson et al. |
| 5,797,905 A | 8/1998 | Fleischman et al. |

(56) References Cited

U.S. PATENT DOCUMENTS

| | | |
|---|---|---|
| 5,800,378 A | 9/1998 | Edwards et al. |
| 5,800,432 A | 9/1998 | Swanson |
| 5,807,309 A | 9/1998 | Lundquist et al. |
| 5,807,395 A | 9/1998 | Mulier et al. |
| 5,810,802 A | 9/1998 | Panescu et al. |
| 5,810,804 A | 9/1998 | Gough et al. |
| 5,823,955 A | 10/1998 | Kuck et al. |
| 5,827,277 A | 10/1998 | Edwards |
| 5,830,213 A | 11/1998 | Panescu et al. |
| 5,833,621 A | 11/1998 | Panescu et al. |
| 5,833,688 A | 11/1998 | Sieben et al. |
| 5,836,874 A | 11/1998 | Swanson et al. |
| 5,836,947 A | 11/1998 | Fleischman et al. |
| 5,836,990 A | 11/1998 | Li |
| 5,837,001 A | 11/1998 | Mackey |
| 5,840,076 A | 11/1998 | Swanson et al. |
| 5,846,238 A | 12/1998 | Jackson et al. |
| 5,846,239 A | 12/1998 | Swanson et al. |
| 5,848,969 A | 12/1998 | Panescu et al. |
| 5,849,028 A | 12/1998 | Chen |
| 5,853,409 A | 12/1998 | Swanson et al. |
| 5,853,411 A | 12/1998 | Whayne et al. |
| 5,863,290 A | 1/1999 | Gough et al. |
| 5,865,800 A | 2/1999 | Mirarchi et al. |
| 5,868,736 A | 2/1999 | Swanson et al. |
| 5,868,743 A | 2/1999 | Saul et al. |
| 5,871,483 A | 2/1999 | Jackson et al. |
| 5,876,336 A | 3/1999 | Swanson et al. |
| 5,876,340 A | 3/1999 | Tu et al. |
| 5,879,348 A | 3/1999 | Owens et al. |
| 5,879,349 A | 3/1999 | Edwards |
| 5,891,136 A | 4/1999 | McGee et al. |
| 5,893,885 A | 4/1999 | Webster, Jr. |
| 5,897,552 A | 4/1999 | Edwards et al. |
| 5,904,651 A | 5/1999 | Swanson et al. |
| 5,904,680 A | 5/1999 | Kordis et al. |
| 5,904,709 A | 5/1999 | Arndt et al. |
| 5,906,590 A | 5/1999 | Hunjan et al. |
| 5,906,614 A | 5/1999 | Stern et al. |
| 5,908,445 A | 6/1999 | Whayne et al. |
| 5,910,129 A | 6/1999 | Koblish et al. |
| 5,911,739 A | 6/1999 | Kordis et al. |
| 5,913,856 A | 6/1999 | Chia et al. |
| 5,916,163 A | 6/1999 | Panescu et al. |
| 5,919,218 A | 7/1999 | Carr |
| 5,925,038 A | 7/1999 | Panescu et al. |
| 5,928,228 A | 7/1999 | Kordis et al. |
| 5,928,229 A | 7/1999 | Gough et al. |
| 5,933,672 A | 8/1999 | Huang |
| 5,935,063 A | 8/1999 | Nguyen |
| 5,935,079 A | 8/1999 | Swanson et al. |
| 5,935,124 A | 8/1999 | Klumb et al. |
| 5,938,658 A | 8/1999 | Tu |
| 5,938,659 A | 8/1999 | Tu et al. |
| 5,941,251 A | 8/1999 | Panescu et al. |
| 5,948,009 A | 9/1999 | Tu |
| 5,954,661 A | 9/1999 | Greenspon et al. |
| 5,954,662 A | 9/1999 | Swanson et al. |
| 5,954,719 A | 9/1999 | Chen et al. |
| 5,957,863 A | 9/1999 | Koblish et al. |
| 5,957,922 A | 9/1999 | Imran |
| 5,957,961 A | 9/1999 | Maguire et al. |
| 5,961,513 A | 10/1999 | Swanson et al. |
| 5,964,727 A | 10/1999 | Edwards et al. |
| 5,967,976 A | 10/1999 | Larsen et al. |
| 5,968,040 A | 10/1999 | Swanson et al. |
| 5,971,980 A | 10/1999 | Sherman |
| 5,974,343 A | 10/1999 | Brevard et al. |
| 5,980,517 A | 11/1999 | Gough |
| 5,983,124 A | 11/1999 | Carr |
| 5,991,650 A | 11/1999 | Swanson et al. |
| 5,992,419 A | 11/1999 | Sterzer et al. |
| 5,997,534 A | 12/1999 | Tu et al. |
| 6,006,123 A | 12/1999 | Nguyen et al. |
| 6,009,351 A | 12/1999 | Flachman |
| 6,014,581 A | 1/2000 | Whayne et al. |
| 6,014,590 A | 1/2000 | Whayne et al. |
| 6,022,346 A | 2/2000 | Panescu et al. |
| 6,030,379 A | 2/2000 | Panescu et al. |
| 6,030,382 A | 2/2000 | Fleischman et al. |
| 6,032,061 A | 2/2000 | Koblish |
| 6,035,226 A | 3/2000 | Panescu |
| 6,047,218 A | 4/2000 | Whayne et al. |
| 6,048,329 A | 4/2000 | Thompson et al. |
| 6,049,732 A | 4/2000 | Panescu et al. |
| 6,053,912 A | 4/2000 | Panescu et al. |
| 6,056,745 A | 5/2000 | Panescu et al. |
| 6,059,780 A | 5/2000 | Gough et al. |
| 6,063,078 A | 5/2000 | Wittkampf |
| 6,070,094 A | 5/2000 | Swanson et al. |
| 6,071,278 A | 6/2000 | Panescu et al. |
| 6,076,012 A | 6/2000 | Swanson et al. |
| 6,080,150 A | 6/2000 | Gough |
| 6,083,222 A | 7/2000 | Klein et al. |
| 6,086,532 A | 7/2000 | Panescu et al. |
| 6,090,105 A | 7/2000 | Zepeda et al. |
| 6,095,150 A | 8/2000 | Panescu et al. |
| 6,097,976 A | 8/2000 | Yang et al. |
| 6,101,409 A | 8/2000 | Swanson et al. |
| 6,101,410 A | 8/2000 | Panescu et al. |
| 6,106,460 A | 8/2000 | Panescu et al. |
| 6,106,522 A | 8/2000 | Fleischman et al. |
| 6,113,591 A | 9/2000 | Whayne et al. |
| 6,113,593 A | 9/2000 | Tu et al. |
| 6,115,626 A | 9/2000 | Whayne et al. |
| 6,123,702 A | 9/2000 | Swanson et al. |
| 6,123,703 A | 9/2000 | Tu et al. |
| 6,129,669 A | 10/2000 | Panescu et al. |
| 6,129,724 A | 10/2000 | Fleischman et al. |
| 6,132,425 A | 10/2000 | Gough |
| 6,142,994 A | 11/2000 | Swanson et al. |
| 6,146,359 A | 11/2000 | Carr et al. |
| 6,162,184 A | 12/2000 | Swanson et al. |
| 6,165,169 A | 12/2000 | Panescu et al. |
| 6,171,275 B1 | 1/2001 | Webster, Jr. |
| 6,171,306 B1 | 1/2001 | Swanson et al. |
| 6,179,835 B1 | 1/2001 | Panescu et al. |
| 6,183,468 B1 | 2/2001 | Swanson et al. |
| 6,188,924 B1 | 2/2001 | Swanson et al. |
| 6,192,266 B1 | 2/2001 | Dupree et al. |
| 6,193,713 B1 | 2/2001 | Geistert et al. |
| 6,197,021 B1 | 3/2001 | Panescu et al. |
| 6,206,831 B1 | 3/2001 | Suorsa et al. |
| 6,210,367 B1 | 4/2001 | Carr |
| 6,210,406 B1 | 4/2001 | Webster |
| 6,216,043 B1 | 4/2001 | Swanson et al. |
| 6,217,528 B1 | 4/2001 | Koblish et al. |
| 6,217,573 B1 | 4/2001 | Webster |
| 6,217,574 B1 | 4/2001 | Webster |
| 6,217,576 B1 | 4/2001 | Tu et al. |
| 6,221,013 B1 | 4/2001 | Panescu et al. |
| 6,230,060 B1 | 5/2001 | Mawhinney |
| 6,235,022 B1 | 5/2001 | Hallock et al. |
| 6,235,023 B1 | 5/2001 | Lee et al. |
| 6,238,389 B1 | 5/2001 | Paddock et al. |
| 6,245,061 B1 | 6/2001 | Panescu et al. |
| 6,245,065 B1 | 6/2001 | Panescu et al. |
| 6,251,107 B1 | 6/2001 | Schaer |
| 6,256,525 B1 | 7/2001 | Yang et al. |
| 6,256,540 B1 | 7/2001 | Panescu et al. |
| 6,259,941 B1 | 7/2001 | Chia et al. |
| 6,277,113 B1 | 8/2001 | Berube |
| 6,283,962 B1 | 9/2001 | Tu et al. |
| 6,289,239 B1 | 9/2001 | Panescu et al. |
| 6,293,943 B1 | 9/2001 | Panescu et al. |
| 6,309,385 B1 | 10/2001 | Simpson |
| 6,330,473 B1 | 12/2001 | Swanson et al. |
| 6,346,104 B2 | 2/2002 | Daly et al. |
| 6,350,262 B1 | 2/2002 | Ashley |
| 6,352,534 B1 | 3/2002 | Paddock et al. |
| 6,353,751 B1 | 3/2002 | Swanson et al. |
| 6,356,790 B1 | 3/2002 | Maguire et al. |
| 6,357,447 B1 | 3/2002 | Swanson et al. |
| 6,364,876 B1 | 4/2002 | Erb et al. |

(56) References Cited

U.S. PATENT DOCUMENTS

| | | |
|---|---|---|
| 6,370,435 B2 | 4/2002 | Panescu et al. |
| 6,371,955 B1 | 4/2002 | Fuimaono et al. |
| 6,389,311 B1 | 5/2002 | Whayne et al. |
| 6,391,024 B1 | 5/2002 | Sun et al. |
| 6,402,739 B1 | 6/2002 | Neev |
| 6,402,742 B1 | 6/2002 | Blewett et al. |
| 6,405,067 B1 | 6/2002 | Mest et al. |
| 6,423,057 B1 | 7/2002 | He et al. |
| 6,424,869 B1 | 7/2002 | Carr et al. |
| 6,425,895 B1 | 7/2002 | Swanson et al. |
| 6,428,536 B2 | 8/2002 | Panescu et al. |
| 6,440,129 B1 | 8/2002 | Simpson |
| 6,445,957 B1 | 9/2002 | Bolmsjo |
| 6,456,864 B1 | 9/2002 | Swanson et al. |
| 6,458,123 B1 | 10/2002 | Brucker et al. |
| 6,463,331 B1 | 10/2002 | Edwards |
| 6,464,700 B1 | 10/2002 | Koblish et al. |
| 6,468,272 B1 | 10/2002 | Koblish et al. |
| 6,470,219 B1 | 10/2002 | Edwards et al. |
| 6,471,699 B1 | 10/2002 | Fleischman et al. |
| 6,477,396 B1 | 11/2002 | Mest et al. |
| 6,477,426 B1 | 11/2002 | Fenn et al. |
| 6,482,203 B2 | 11/2002 | Paddock et al. |
| 6,487,441 B1 | 11/2002 | Swanson et al. |
| 6,488,679 B1 | 12/2002 | Swanson et al. |
| 6,490,488 B1 | 12/2002 | Rudie et al. |
| 6,494,880 B1 | 12/2002 | Swanson et al. |
| 6,496,738 B2 | 12/2002 | Carr |
| 6,500,172 B1 | 12/2002 | Panescu et al. |
| 6,500,175 B1 | 12/2002 | Gough et al. |
| 6,508,765 B2 | 1/2003 | Suorsa et al. |
| 6,511,478 B1 | 1/2003 | Burnside et al. |
| 6,514,249 B1 | 2/2003 | Maguire et al. |
| 6,514,250 B1 | 2/2003 | Jahns et al. |
| 6,516,807 B1 | 2/2003 | Panescu et al. |
| 6,522,913 B2 | 2/2003 | Swanson et al. |
| 6,522,930 B1 | 2/2003 | Schaer et al. |
| 6,522,931 B2 | 2/2003 | Manker et al. |
| 6,529,756 B1 | 3/2003 | Phan et al. |
| 6,537,272 B2 | 3/2003 | Christopherson et al. |
| 6,542,773 B2 | 4/2003 | Dupree et al. |
| 6,542,781 B1 | 4/2003 | Koblish et al. |
| 6,565,511 B2 | 5/2003 | Panescu et al. |
| 6,577,902 B1 | 6/2003 | Laufer et al. |
| 6,579,288 B1 | 6/2003 | Swanson et al. |
| 6,582,425 B2 | 6/2003 | Simpson |
| 6,584,360 B2 | 6/2003 | Francischelli et al. |
| 6,587,732 B1 | 7/2003 | Carr |
| 6,597,955 B2 | 7/2003 | Panescu et al. |
| 6,602,242 B1 | 8/2003 | Fung et al. |
| 6,607,505 B1 | 8/2003 | Thompson et al. |
| 6,610,055 B1 | 8/2003 | Swanson et al. |
| 6,611,699 B2 | 8/2003 | Messing |
| 6,613,046 B1 | 9/2003 | Jenkins et al. |
| 6,615,073 B1 | 9/2003 | Panescu et al. |
| 6,616,657 B2 | 9/2003 | Simpson et al. |
| 6,625,482 B1 | 9/2003 | Panescu et al. |
| 6,632,221 B1 | 10/2003 | Edwards et al. |
| 6,632,222 B1 | 10/2003 | Edwards et al. |
| 6,635,056 B2 | 10/2003 | Kadhiresan et al. |
| 6,645,200 B1 | 11/2003 | Koblish et al. |
| 6,652,513 B2 | 11/2003 | Panescu et al. |
| 6,652,516 B1 | 11/2003 | Gough |
| 6,658,279 B2 | 12/2003 | Swanson et al. |
| 6,668,198 B2 | 12/2003 | Swanson et al. |
| 6,669,692 B1 | 12/2003 | Nelson et al. |
| 6,685,702 B2 | 2/2004 | Quijano et al. |
| 6,689,127 B1 | 2/2004 | Gough et al. |
| 6,692,490 B1 | 2/2004 | Edwards |
| 6,699,241 B2 | 3/2004 | Rappaport et al. |
| 6,706,038 B2 | 3/2004 | Francischelli et al. |
| 6,711,444 B2 | 3/2004 | Koblish |
| 6,735,465 B2 | 5/2004 | Panescu |
| 6,736,811 B2 | 5/2004 | Panescu et al. |
| 6,740,040 B1 | 5/2004 | Mandrusov et al. |
| 6,743,197 B1 | 6/2004 | Edwards |
| 6,743,225 B2 | 6/2004 | Sanchez et al. |
| 6,745,080 B2 | 6/2004 | Koblish |
| 6,746,401 B2 | 6/2004 | Panescu |
| 6,752,804 B2 | 6/2004 | Simpson et al. |
| 6,752,805 B2 | 6/2004 | Maguire et al. |
| 6,770,070 B1 | 8/2004 | Balbierz |
| 6,786,905 B2 | 9/2004 | Swanson et al. |
| 6,788,969 B2 | 9/2004 | Dupree et al. |
| 6,788,977 B2 | 9/2004 | Fenn et al. |
| 6,790,206 B2 | 9/2004 | Panescu |
| 6,805,129 B1 | 10/2004 | Pless et al. |
| 6,814,730 B2 | 11/2004 | Li |
| 6,823,216 B1 | 11/2004 | Salomir et al. |
| 6,824,515 B2 | 11/2004 | Suorsa et al. |
| 6,837,885 B2 | 1/2005 | Koblish et al. |
| 6,840,936 B2 | 1/2005 | Sliwa, Jr. et al. |
| 6,847,848 B2 | 1/2005 | Sterzer et al. |
| 6,849,073 B2 | 2/2005 | Hoey et al. |
| 6,852,120 B1 | 2/2005 | Fuimaono |
| 6,887,238 B2 | 5/2005 | Jahns et al. |
| 6,888,141 B2 | 5/2005 | Carr |
| 6,895,267 B2 | 5/2005 | Panescu et al. |
| 6,904,303 B2 | 6/2005 | Phan et al. |
| 6,905,495 B1 | 6/2005 | Fuimaono et al. |
| 6,917,834 B2 | 7/2005 | Koblish et al. |
| 6,932,776 B2 | 8/2005 | Carr |
| 6,936,047 B2 | 8/2005 | Nasab et al. |
| 6,949,095 B2 | 9/2005 | Vaska et al. |
| 6,953,460 B2 | 10/2005 | Maguire et al. |
| 6,958,075 B2 | 10/2005 | Mon et al. |
| 6,960,205 B2 | 11/2005 | Jahns et al. |
| 6,974,455 B2 | 12/2005 | Garabedian et al. |
| 6,976,492 B2 | 12/2005 | Ingle et al. |
| 6,979,329 B2 | 12/2005 | Burnside et al. |
| 6,986,769 B2 | 1/2006 | Nelson et al. |
| 7,001,383 B2 | 2/2006 | Keidar |
| 7,008,417 B2 | 3/2006 | Eick |
| 7,029,470 B2 | 4/2006 | Francischelli et al. |
| 7,052,492 B2 | 5/2006 | Swanson et al. |
| 7,150,744 B2 | 12/2006 | Edwards et al. |
| 7,151,964 B2 | 12/2006 | Desai et al. |
| 7,160,296 B2 | 1/2007 | Pearson et al. |
| 7,163,537 B2 | 1/2007 | Lee et al. |
| 7,166,075 B2 | 1/2007 | Varghese et al. |
| 7,175,619 B2 | 2/2007 | Koblish et al. |
| 7,175,734 B2 | 2/2007 | Stewart et al. |
| 7,184,811 B2 | 2/2007 | Phan et al. |
| 7,186,250 B2 | 3/2007 | Koblish et al. |
| 7,194,294 B2 | 3/2007 | Panescu et al. |
| 7,197,356 B2 | 3/2007 | Carr |
| 7,252,664 B2 | 8/2007 | Nasab et al. |
| 7,263,398 B2 | 8/2007 | Carr |
| 7,276,061 B2 | 10/2007 | Schaer et al. |
| 7,285,116 B2 | 10/2007 | de la Rama et al. |
| 7,303,558 B2 | 12/2007 | Swanson |
| 7,306,593 B2 | 12/2007 | Keidar et al. |
| 7,326,235 B2 | 2/2008 | Edwards |
| 7,331,960 B2 | 2/2008 | Schaer |
| 7,344,533 B2 | 3/2008 | Pearson et al. |
| 7,364,546 B2 | 4/2008 | Panescu et al. |
| 7,367,972 B2 | 5/2008 | Francischelli et al. |
| 7,371,233 B2 | 5/2008 | Swanson et al. |
| 7,435,248 B2 | 10/2008 | Taimisto et al. |
| 7,474,909 B2 | 1/2009 | Phan et al. |
| 7,565,208 B2 | 7/2009 | Harris et al. |
| 7,582,050 B2 | 9/2009 | Schlorff et al. |
| 7,582,084 B2 | 9/2009 | Swanson et al. |
| 7,588,568 B2 | 9/2009 | Fuimaono et al. |
| 7,588,658 B2 | 9/2009 | Yamamoto et al. |
| 7,623,899 B2 | 11/2009 | Worley et al. |
| 7,628,788 B2 | 12/2009 | Datta |
| 7,662,152 B2 | 2/2010 | Sharareh et al. |
| 7,670,336 B2 | 3/2010 | Young et al. |
| 7,676,264 B1 | 3/2010 | Pillai et al. |
| 7,678,104 B2 | 3/2010 | Keidar |
| 7,699,829 B2 | 4/2010 | Harris et al. |
| 7,699,841 B2 | 4/2010 | Carr |
| 7,727,230 B2 | 6/2010 | Fuimaono et al. |

(56) References Cited

U.S. PATENT DOCUMENTS

| | | |
|---|---|---|
| 7,734,330 B2 | 6/2010 | Carr |
| 7,761,148 B2 | 7/2010 | Fuimaono et al. |
| 7,764,994 B2 | 7/2010 | Fuimaono et al. |
| 7,766,907 B2 | 8/2010 | Dando et al. |
| 7,769,469 B2 | 8/2010 | Carr et al. |
| 7,771,418 B2 | 8/2010 | Chopra et al. |
| 7,771,420 B2 | 8/2010 | Butty et al. |
| 7,774,039 B2 | 8/2010 | Koblish |
| 7,794,404 B1 | 9/2010 | Gutfinger et al. |
| 7,794,460 B2 | 9/2010 | Mulier et al. |
| 7,811,313 B2 | 10/2010 | Mon et al. |
| 7,815,635 B2 | 10/2010 | Wittkampf et al. |
| 7,824,399 B2 | 11/2010 | Francischelli et al. |
| 7,826,904 B2 | 11/2010 | Appling et al. |
| 7,833,220 B2 | 11/2010 | Mon et al. |
| 7,837,720 B2 | 11/2010 | Mon |
| 7,857,809 B2 | 12/2010 | Drysen |
| 7,857,810 B2 | 12/2010 | Wang et al. |
| 7,862,563 B1 | 1/2011 | Cosman et al. |
| 7,867,227 B2 | 1/2011 | Slater |
| 7,879,029 B2 | 2/2011 | Jimenez |
| 7,918,850 B2 | 4/2011 | Govari et al. |
| 7,918,851 B2 | 4/2011 | Webster, Jr. et al. |
| 7,925,341 B2 | 4/2011 | Fuimaono |
| 7,925,349 B1 | 4/2011 | Wong et al. |
| 7,927,328 B2 | 4/2011 | Orszulak et al. |
| 7,933,660 B2 | 4/2011 | Carr |
| 7,938,828 B2 | 5/2011 | Koblish |
| 7,945,326 B1 | 5/2011 | Wong et al. |
| 7,946,995 B1 | 5/2011 | Koh et al. |
| 7,955,369 B2 | 6/2011 | Thompson et al. |
| 7,957,813 B1 | 6/2011 | Persson et al. |
| 7,959,628 B2 | 6/2011 | Schaer et al. |
| 7,959,630 B2 | 6/2011 | Taimisto et al. |
| 7,963,925 B1 | 6/2011 | Schecter |
| 7,967,817 B2 | 6/2011 | Anderson et al. |
| 7,976,537 B2 | 7/2011 | Lieber et al. |
| 7,989,741 B2 | 8/2011 | Carr |
| 7,996,078 B2 | 8/2011 | Paul et al. |
| 7,998,140 B2 | 8/2011 | McClurken et al. |
| 7,998,141 B2 | 8/2011 | Wittkampf et al. |
| 8,002,770 B2 | 8/2011 | Swanson et al. |
| 8,007,497 B2 | 8/2011 | Young et al. |
| 8,010,196 B1 | 8/2011 | Wong et al. |
| 8,011,055 B2 | 9/2011 | Lesley |
| 8,012,150 B2 | 9/2011 | Wham et al. |
| 8,019,419 B1 | 9/2011 | Panescu et al. |
| 8,032,218 B2 | 10/2011 | Wong et al. |
| 8,034,050 B2 | 10/2011 | Sharareh et al. |
| 8,034,052 B2 | 10/2011 | Podhajsky |
| 8,038,670 B2 | 10/2011 | McClurken |
| 8,048,070 B2 | 11/2011 | O'Brien et al. |
| 8,052,684 B2 | 11/2011 | Wang et al. |
| 8,062,228 B2 | 11/2011 | Carr |
| 8,065,005 B1 | 11/2011 | Wong et al. |
| 8,083,736 B2 | 12/2011 | McClurken et al. |
| 8,100,895 B2 | 1/2012 | Panos et al. |
| 8,104,956 B2 | 1/2012 | Blaha |
| 8,118,809 B2 | 2/2012 | Paul et al. |
| 8,123,745 B2 | 2/2012 | Beeckler et al. |
| 8,128,617 B2 | 3/2012 | Bencini et al. |
| 8,133,220 B2 | 3/2012 | Lee et al. |
| 8,145,289 B2 | 3/2012 | Calabro" et al. |
| 8,152,801 B2 | 4/2012 | Goldberg et al. |
| 8,157,796 B2 | 4/2012 | Collins et al. |
| 8,160,693 B2 | 4/2012 | Fuimaono |
| 8,175,680 B2 | 5/2012 | Panescu |
| 8,192,424 B2 | 6/2012 | Woloszko |
| 8,202,224 B2 | 6/2012 | Gutfinger et al. |
| 8,206,380 B2 | 6/2012 | Lenihan et al. |
| 8,208,999 B2 | 6/2012 | Wenzel et al. |
| 8,211,099 B2 | 7/2012 | Buysse et al. |
| 8,216,216 B2 | 7/2012 | Warnking et al. |
| 8,221,413 B2 | 7/2012 | Mon et al. |
| 8,221,414 B2 | 7/2012 | Mon et al. |
| 8,224,455 B2 | 7/2012 | Mon et al. |
| 8,226,645 B2 | 7/2012 | Harrington et al. |
| 8,229,538 B2 | 7/2012 | Koblish |
| 8,256,428 B2 | 9/2012 | Hindricks et al. |
| 8,262,652 B2 | 9/2012 | Podhajsky |
| 8,262,653 B2 | 9/2012 | Plaza |
| 8,265,747 B2 | 9/2012 | Rittman, III et al. |
| 8,267,926 B2 | 9/2012 | Paul et al. |
| 8,267,929 B2 | 9/2012 | Wham et al. |
| 8,267,932 B2 | 9/2012 | Baxter et al. |
| 8,280,511 B2 | 10/2012 | Zhao et al. |
| 8,287,532 B2 | 10/2012 | Carroll et al. |
| 8,287,533 B2 | 10/2012 | Wittkampf et al. |
| 8,290,578 B2 | 10/2012 | Schneider |
| 8,298,223 B2 | 10/2012 | Wham et al. |
| 8,298,227 B2 | 10/2012 | Leo et al. |
| 8,303,172 B2 | 11/2012 | Zei et al. |
| 8,303,580 B2 | 11/2012 | Wham et al. |
| 8,306,623 B2 | 11/2012 | Wong et al. |
| 8,308,719 B2 | 11/2012 | Sliwa et al. |
| 8,317,783 B2 | 11/2012 | Cao et al. |
| 8,321,019 B2 | 11/2012 | Esch et al. |
| 8,333,759 B2 | 12/2012 | Podhajsky |
| 8,333,762 B2 | 12/2012 | Mest et al. |
| 8,359,092 B2 | 1/2013 | Hayam et al. |
| 8,369,922 B2 | 2/2013 | Paul et al. |
| 8,372,066 B2 | 2/2013 | Manwaring et al. |
| 8,374,670 B2 | 2/2013 | Selkee |
| 8,374,702 B2 | 2/2013 | Mon et al. |
| 8,377,052 B2 | 2/2013 | Manwaring et al. |
| 8,380,275 B2 | 2/2013 | Kim et al. |
| 8,386,049 B2 | 2/2013 | Persson et al. |
| 8,398,623 B2 | 3/2013 | Warnking et al. |
| 8,403,925 B2 | 3/2013 | Miller et al. |
| 8,406,866 B2 | 3/2013 | Deno et al. |
| 8,409,191 B2 | 4/2013 | Avitall et al. |
| 8,409,192 B2 | 4/2013 | Asirvatham et al. |
| 8,414,570 B2 | 4/2013 | Turner et al. |
| 8,414,579 B2 | 4/2013 | Kim et al. |
| 8,419,725 B2 | 4/2013 | Haemmerich et al. |
| 8,423,115 B2 | 4/2013 | Koblish |
| 8,440,949 B2 | 5/2013 | Carr |
| 8,442,613 B2 | 5/2013 | Kim et al. |
| 8,444,637 B2 | 5/2013 | Podmore et al. |
| 8,449,535 B2 | 5/2013 | Deno et al. |
| 8,449,537 B2 | 5/2013 | Cao et al. |
| 8,449,539 B2 | 5/2013 | Wang et al. |
| 8,460,285 B2 | 6/2013 | Wang et al. |
| 8,473,023 B2 | 6/2013 | Worley et al. |
| 8,475,448 B2 | 7/2013 | Sharareh et al. |
| 8,475,450 B2 | 7/2013 | Govari et al. |
| 8,480,663 B2 | 7/2013 | Ingle et al. |
| 8,480,666 B2 | 7/2013 | Buysse et al. |
| 8,486,065 B2 | 7/2013 | Lee et al. |
| 8,491,578 B2 | 7/2013 | Manwaring et al. |
| 8,504,152 B2 | 8/2013 | Wenzel et al. |
| 8,504,153 B2 | 8/2013 | Wenzel et al. |
| 8,515,554 B2 | 8/2013 | Carr |
| 8,517,999 B2 | 8/2013 | Pappone et al. |
| 8,523,851 B2 | 9/2013 | Manwaring et al. |
| 8,523,852 B2 | 9/2013 | Manwaring et al. |
| 8,535,303 B2 | 9/2013 | Avitall et al. |
| 8,545,409 B2 | 10/2013 | Sliwa et al. |
| 8,554,333 B2 | 10/2013 | Wu et al. |
| 8,556,893 B2 | 10/2013 | Potter |
| 8,562,600 B2 | 10/2013 | Kirkpatrick et al. |
| 8,568,402 B2 | 10/2013 | Buysse et al. |
| 8,574,166 B2 | 11/2013 | Carr |
| 8,600,472 B2 | 12/2013 | Govari et al. |
| 8,600,497 B1 | 12/2013 | Yang et al. |
| 8,603,084 B2 | 12/2013 | Fish et al. |
| 8,628,520 B2 | 1/2014 | Sharareh et al. |
| 8,632,533 B2 | 1/2014 | Greeley et al. |
| 8,636,729 B2 | 1/2014 | Esch et al. |
| 8,641,708 B2 | 2/2014 | Govari et al. |
| 8,663,122 B2 | 3/2014 | Schecter |
| 8,668,686 B2 | 3/2014 | Govari et al. |
| 8,696,659 B2 | 4/2014 | Marion |
| 8,700,120 B2 | 4/2014 | Koblish |

(56) References Cited

U.S. PATENT DOCUMENTS

| | | | |
|---|---|---|---|
| 8,702,690 B2 | 4/2014 | Paul et al. |
| 8,702,693 B2 | 4/2014 | Subramaniam et al. |
| 8,712,519 B1 | 4/2014 | Panescu et al. |
| 8,721,634 B2 | 5/2014 | Esch et al. |
| 8,725,228 B2 | 5/2014 | Koblish et al. |
| 8,728,074 B2 | 5/2014 | West et al. |
| 8,728,077 B2 | 5/2014 | Paul et al. |
| 8,731,631 B2 | 5/2014 | Kim et al. |
| 8,731,684 B2 | 5/2014 | Carr et al. |
| 8,734,442 B2 | 5/2014 | Cao et al. |
| 8,740,900 B2 | 6/2014 | Kim et al. |
| 8,755,860 B2 | 6/2014 | Paul et al. |
| 8,764,746 B2 | 7/2014 | Podmore et al. |
| 8,777,942 B2 | 7/2014 | Wu et al. |
| 8,784,414 B2 | 7/2014 | Avitall et al. |
| 8,792,958 B2 | 7/2014 | Kim et al. |
| 8,795,271 B2 | 8/2014 | Koblish et al. |
| 8,798,706 B2 | 8/2014 | Kim et al. |
| 8,814,824 B2 | 8/2014 | Kauphusman et al. |
| 8,814,857 B2 | 8/2014 | Christian |
| 8,834,388 B2 | 9/2014 | Sherman |
| 8,834,461 B2 | 9/2014 | Werneth et al. |
| 8,845,629 B2 | 9/2014 | Demarais et al. |
| 8,845,633 B2 | 9/2014 | Wang et al. |
| 8,858,548 B2 | 10/2014 | Asconeguy |
| 8,868,165 B1 | 10/2014 | Nabutovsky et al. |
| 8,876,817 B2 | 11/2014 | Avitall et al. |
| 8,876,819 B2 | 11/2014 | Tegg et al. |
| 8,882,755 B2 | 11/2014 | Leung et al. |
| 8,882,759 B2 | 11/2014 | Manley et al. |
| 8,882,761 B2 | 11/2014 | Desai |
| 8,900,225 B2 | 12/2014 | Bar-Tal et al. |
| 8,900,228 B2 | 12/2014 | Grunewald et al. |
| 8,906,010 B2 | 12/2014 | Edwards et al. |
| 8,920,415 B2 | 12/2014 | Govari |
| 8,926,605 B2 | 1/2015 | McCarthy et al. |
| 8,932,284 B2 | 1/2015 | McCarthy et al. |
| 8,934,953 B2 | 1/2015 | Carr et al. |
| 8,942,828 B1 | 1/2015 | Schecter |
| 8,945,015 B2 | 2/2015 | Rankin et al. |
| 8,954,161 B2 | 2/2015 | McCarthy et al. |
| 8,956,304 B2 | 2/2015 | Schecter |
| 8,961,506 B2 | 2/2015 | McCarthy et al. |
| 8,992,519 B2 | 3/2015 | Kim et al. |
| 8,998,890 B2 | 4/2015 | Paul et al. |
| 9,014,814 B2 | 4/2015 | McCarthy et al. |
| 9,023,030 B2 | 5/2015 | Koblish et al. |
| 9,060,756 B2 | 6/2015 | Bencini et al. |
| 9,066,662 B2 | 6/2015 | Wenzel et al. |
| 9,089,340 B2 | 7/2015 | Hastings et al. |
| 9,095,349 B2 | 8/2015 | Fish et al. |
| 9,173,586 B2 | 11/2015 | Deno et al. |
| 9,179,972 B2 | 11/2015 | Olson |
| 9,204,927 B2 | 12/2015 | Afonso et al. |
| 9,226,791 B2 | 1/2016 | McCarthy et al. |
| 9,254,163 B2 | 2/2016 | Paul et al. |
| 9,265,574 B2 | 2/2016 | Bar-Tal et al. |
| 9,271,782 B2 | 3/2016 | Paul et al. |
| 9,277,961 B2 | 3/2016 | Panescu et al. |
| 9,283,025 B2 | 3/2016 | Paul et al. |
| 9,283,026 B2 | 3/2016 | Paul et al. |
| 9,364,282 B2 | 6/2016 | Just et al. |
| 9,456,867 B2 | 10/2016 | Lawrence et al. |
| 9,474,458 B2 | 10/2016 | Clark et al. |
| 2001/0001830 A1 | 5/2001 | Dobak et al. |
| 2001/0007927 A1 | 7/2001 | Koblish et al. |
| 2002/0004631 A1 | 1/2002 | Jenkins et al. |
| 2002/0022829 A1 | 2/2002 | Nagase et al. |
| 2002/0026185 A1 | 2/2002 | Gough |
| 2002/0040229 A1 | 4/2002 | Norman |
| 2002/0058870 A1 | 5/2002 | Panescu et al. |
| 2002/0065465 A1 | 5/2002 | Panescu et al. |
| 2002/0115941 A1 | 8/2002 | Whayne et al. |
| 2002/0128636 A1 | 9/2002 | Chin et al. |
| 2002/0128639 A1 | 9/2002 | Pless et al. |
| 2002/0128643 A1 | 9/2002 | Simpson et al. |
| 2002/0165529 A1 | 11/2002 | Danek |
| 2002/0169444 A1 | 11/2002 | Mest et al. |
| 2002/0183736 A1 | 12/2002 | Francischelli et al. |
| 2002/0193790 A1 | 12/2002 | Fleischman et al. |
| 2002/0198520 A1 | 12/2002 | Coen et al. |
| 2003/0014049 A1 | 1/2003 | Koblish et al. |
| 2003/0050557 A1 | 3/2003 | Susil et al. |
| 2003/0055470 A1 | 3/2003 | Mon et al. |
| 2003/0065322 A1 | 4/2003 | Panescu et al. |
| 2003/0069619 A1 | 4/2003 | Fenn et al. |
| 2003/0078494 A1* | 4/2003 | Panescu ................. A61B 5/06 600/424 |
| 2003/0078509 A1 | 4/2003 | Panescu |
| 2003/0078573 A1 | 4/2003 | Truckai et al. |
| 2003/0088244 A1 | 5/2003 | Swanson et al. |
| 2003/0093067 A1 | 5/2003 | Panescu |
| 2003/0120171 A1 | 6/2003 | Diamantopoulos et al. |
| 2003/0153967 A1 | 8/2003 | Koblish et al. |
| 2003/0195406 A1 | 10/2003 | Jenkins et al. |
| 2003/0199817 A1 | 10/2003 | Thompson et al. |
| 2004/0054272 A1 | 3/2004 | Messing |
| 2004/0092806 A1 | 5/2004 | Sagon et al. |
| 2004/0097803 A1 | 5/2004 | Panescu |
| 2004/0138656 A1 | 7/2004 | Francischelli et al. |
| 2004/0147915 A1 | 7/2004 | Hasebe |
| 2004/0260278 A1 | 12/2004 | Anderson et al. |
| 2005/0015082 A1 | 1/2005 | O'Sullivan et al. |
| 2005/0033221 A1 | 2/2005 | Fiumaono |
| 2005/0059963 A1 | 3/2005 | Phan et al. |
| 2005/0143727 A1 | 6/2005 | Koblish et al. |
| 2005/0177151 A1 | 8/2005 | Coen et al. |
| 2005/0197657 A1 | 9/2005 | Goth et al. |
| 2005/0228370 A1 | 10/2005 | Sterzer et al. |
| 2005/0245949 A1 | 11/2005 | Goth et al. |
| 2005/0251125 A1 | 11/2005 | Pless et al. |
| 2006/0025758 A1 | 2/2006 | Strul et al. |
| 2006/0064083 A1 | 3/2006 | Khalaj et al. |
| 2006/0089688 A1 | 4/2006 | Panescu |
| 2006/0095032 A1 | 5/2006 | Jackson et al. |
| 2006/0135957 A1 | 6/2006 | Panescu |
| 2006/0167445 A1 | 7/2006 | Shafirstein |
| 2006/0184166 A1 | 8/2006 | Valle et al. |
| 2006/0184221 A1 | 8/2006 | Stewart et al. |
| 2006/0217701 A1 | 9/2006 | Young et al. |
| 2006/0247615 A1 | 11/2006 | McCullagh et al. |
| 2006/0253115 A1 | 11/2006 | Avitall et al. |
| 2006/0293731 A1 | 12/2006 | Rubinsky et al. |
| 2007/0032788 A1 | 2/2007 | Edwards et al. |
| 2007/0049925 A1 | 3/2007 | Phan et al. |
| 2007/0055227 A1 | 3/2007 | Khalaj et al. |
| 2007/0055326 A1 | 3/2007 | Farley et al. |
| 2007/0055328 A1 | 3/2007 | Mayse et al. |
| 2007/0066968 A1 | 3/2007 | Rahn |
| 2007/0066972 A1 | 3/2007 | Ormsby et al. |
| 2007/0073286 A1 | 3/2007 | Panescu et al. |
| 2007/0129720 A1 | 6/2007 | Demarais et al. |
| 2007/0135810 A1 | 6/2007 | Lee et al. |
| 2007/0149963 A1 | 6/2007 | Matsukuma et al. |
| 2007/0156114 A1 | 7/2007 | Worley et al. |
| 2007/0179378 A1 | 8/2007 | Boese et al. |
| 2007/0185478 A1 | 8/2007 | Cosentino |
| 2007/0198007 A1 | 8/2007 | Govari et al. |
| 2007/0225697 A1 | 9/2007 | Shroff et al. |
| 2007/0244476 A1 | 10/2007 | Kochamba et al. |
| 2007/0244534 A1 | 10/2007 | Kochamba et al. |
| 2007/0299488 A1 | 12/2007 | Carr |
| 2008/0015563 A1 | 1/2008 | Hoey et al. |
| 2008/0015571 A1 | 1/2008 | Rubinsky et al. |
| 2008/0033300 A1 | 2/2008 | Hoang et al. |
| 2008/0077126 A1 | 3/2008 | Rashidi |
| 2008/0082091 A1 | 4/2008 | Rubtsov et al. |
| 2008/0161797 A1 | 7/2008 | Wang et al. |
| 2008/0172048 A1 | 7/2008 | Martin et al. |
| 2008/0177205 A1 | 7/2008 | Rama et al. |
| 2008/0243112 A1 | 10/2008 | De Neve |
| 2008/0243214 A1 | 10/2008 | Koblish |
| 2008/0249463 A1 | 10/2008 | Pappone et al. |
| 2008/0275440 A1 | 11/2008 | Kratoska et al. |

(56) References Cited

U.S. PATENT DOCUMENTS

| | | |
|---|---|---|
| 2008/0300589 A1 | 12/2008 | Paul et al. |
| 2008/0312521 A1 | 12/2008 | Solomon |
| 2009/0005768 A1 | 1/2009 | Sharareh et al. |
| 2009/0036882 A1 | 2/2009 | Webster et al. |
| 2009/0069808 A1 | 3/2009 | Pike, Jr. et al. |
| 2009/0076409 A1 | 3/2009 | Wu et al. |
| 2009/0093810 A1 | 4/2009 | Subramaniam et al. |
| 2009/0099560 A1 | 4/2009 | Rioux et al. |
| 2009/0118613 A1 | 5/2009 | Krugman et al. |
| 2009/0163916 A1 | 6/2009 | Paul et al. |
| 2009/0177111 A1 | 7/2009 | Miller et al. |
| 2009/0177193 A1 | 7/2009 | Wang et al. |
| 2009/0187183 A1 | 7/2009 | Epstein |
| 2009/0221999 A1 | 9/2009 | Shahidi |
| 2009/0248006 A1 | 10/2009 | Paulus et al. |
| 2009/0254083 A1 | 10/2009 | Wallace et al. |
| 2009/0275827 A1 | 11/2009 | Aiken et al. |
| 2009/0287201 A1 | 11/2009 | Lalonde et al. |
| 2009/0306641 A1 | 12/2009 | Govari et al. |
| 2009/0306643 A1 | 12/2009 | Pappone et al. |
| 2009/0312754 A1 | 12/2009 | Lenihan et al. |
| 2009/0312756 A1 | 12/2009 | Schlesinger et al. |
| 2010/0016848 A1 | 1/2010 | Desai |
| 2010/0023000 A1 | 1/2010 | Stevenson et al. |
| 2010/0030209 A1 | 2/2010 | Govari et al. |
| 2010/0049011 A1 | 2/2010 | Boese et al. |
| 2010/0057072 A1 | 3/2010 | Roman et al. |
| 2010/0057073 A1 | 3/2010 | Roman et al. |
| 2010/0057074 A1 | 3/2010 | Roman et al. |
| 2010/0057080 A1 | 3/2010 | West et al. |
| 2010/0076424 A1 | 3/2010 | Carr |
| 2010/0094271 A1 | 4/2010 | Ward et al. |
| 2010/0114087 A1 | 5/2010 | Edwards et al. |
| 2010/0114227 A1 | 5/2010 | Cholette |
| 2010/0137837 A1 | 6/2010 | Govari et al. |
| 2010/0137857 A1 | 6/2010 | Shroff et al. |
| 2010/0152724 A1 | 6/2010 | Marion et al. |
| 2010/0168570 A1 | 7/2010 | Sliwa et al. |
| 2010/0168571 A1 | 7/2010 | Savery et al. |
| 2010/0168620 A1 | 7/2010 | Klimovitch et al. |
| 2010/0174280 A1 | 7/2010 | Grimaldi |
| 2010/0185191 A1 | 7/2010 | Carr et al. |
| 2010/0198312 A1 | 8/2010 | Stevenson et al. |
| 2010/0204691 A1 | 8/2010 | Bencini |
| 2010/0211070 A1 | 8/2010 | Subramaniam et al. |
| 2010/0217255 A1 | 8/2010 | Greeley et al. |
| 2010/0222859 A1 | 9/2010 | Govari et al. |
| 2010/0286684 A1 | 11/2010 | Hata et al. |
| 2010/0286690 A1 | 11/2010 | Paul et al. |
| 2010/0298823 A1 | 11/2010 | Cao et al. |
| 2010/0331838 A1 | 12/2010 | Ibrahim et al. |
| 2011/0009857 A1 | 1/2011 | Subramaniam et al. |
| 2011/0022041 A1 | 1/2011 | Ingle et al. |
| 2011/0028821 A1 | 2/2011 | Bojovic et al. |
| 2011/0066147 A1 | 3/2011 | He et al. |
| 2011/0077498 A1 | 3/2011 | McDaniel |
| 2011/0105928 A1 | 5/2011 | Bojovic et al. |
| 2011/0112413 A1 | 5/2011 | Panescu et al. |
| 2011/0112414 A1 | 5/2011 | Panescu et al. |
| 2011/0112415 A1 | 5/2011 | Bojovic et al. |
| 2011/0118726 A1 | 5/2011 | de la Rama et al. |
| 2011/0144479 A1 | 6/2011 | Hastings et al. |
| 2011/0144524 A1 | 6/2011 | Fish et al. |
| 2011/0144639 A1 | 6/2011 | Govari |
| 2011/0152853 A1 | 6/2011 | Manley et al. |
| 2011/0160726 A1 | 6/2011 | Ingle |
| 2011/0166472 A1 | 7/2011 | Björling et al. |
| 2011/0172658 A1 | 7/2011 | Gelbart et al. |
| 2011/0184300 A1 | 7/2011 | Shvilkin et al. |
| 2011/0184313 A1 | 7/2011 | Gianchandani et al. |
| 2011/0213356 A1 | 9/2011 | Wright et al. |
| 2011/0224573 A1 | 9/2011 | Bar-Tal et al. |
| 2011/0224664 A1 | 9/2011 | Bar-Tal et al. |
| 2011/0224667 A1 | 9/2011 | Koblish et al. |
| 2011/0257645 A1 | 10/2011 | Thompson et al. |
| 2011/0264000 A1 | 10/2011 | Paul et al. |
| 2011/0264011 A1 | 10/2011 | Wu et al. |
| 2011/0264089 A1 | 10/2011 | Zirkle et al. |
| 2011/0270244 A1 | 11/2011 | Clark et al. |
| 2011/0270246 A1 | 11/2011 | Clark et al. |
| 2011/0282250 A1 | 11/2011 | Fung et al. |
| 2011/0282342 A1 | 11/2011 | Leo et al. |
| 2011/0288544 A1 | 11/2011 | Verin et al. |
| 2011/0295247 A1 | 12/2011 | Schlesinger et al. |
| 2011/0319748 A1 | 12/2011 | Bronskill et al. |
| 2012/0029504 A1 | 2/2012 | Afonson et al. |
| 2012/0029511 A1 | 2/2012 | Smith et al. |
| 2012/0029512 A1 | 2/2012 | Willard et al. |
| 2012/0035603 A1 | 2/2012 | Lenihan |
| 2012/0059368 A1 | 3/2012 | Takaoka et al. |
| 2012/0071870 A1 | 3/2012 | Salahieh |
| 2012/0078138 A1 | 3/2012 | Leo et al. |
| 2012/0089123 A1 | 4/2012 | Organ et al. |
| 2012/0101538 A1 | 4/2012 | Ballakur et al. |
| 2012/0116392 A1 | 5/2012 | Willard |
| 2012/0123411 A1 | 5/2012 | Ibrahim et al. |
| 2012/0130364 A1 | 5/2012 | Besch et al. |
| 2012/0136346 A1 | 5/2012 | Condie et al. |
| 2012/0143097 A1 | 6/2012 | Pike, Jr. |
| 2012/0150170 A1 | 6/2012 | Buysse et al. |
| 2012/0157890 A1 | 6/2012 | Govari et al. |
| 2012/0157990 A1 | 6/2012 | Christian |
| 2012/0165809 A1 | 6/2012 | Christian et al. |
| 2012/0172859 A1 | 7/2012 | Condie et al. |
| 2012/0179068 A1 | 7/2012 | Leo et al. |
| 2012/0189998 A1 | 7/2012 | Kruecker et al. |
| 2012/0197243 A1 | 8/2012 | Sherman et al. |
| 2012/0239019 A1 | 9/2012 | Asconeguy |
| 2012/0245577 A1 | 9/2012 | Mihalik et al. |
| 2012/0265076 A1 | 10/2012 | Schecter |
| 2012/0265137 A1 | 10/2012 | Mon |
| 2012/0265190 A1 | 10/2012 | Curley et al. |
| 2012/0271306 A1 | 10/2012 | Buysse et al. |
| 2012/0277574 A1 | 11/2012 | Panescu |
| 2012/0277737 A1 | 11/2012 | Curley |
| 2012/0283534 A1 | 11/2012 | Carr et al. |
| 2012/0283722 A1 | 11/2012 | Asconeguy |
| 2012/0302877 A1 | 11/2012 | Harks et al. |
| 2012/0303103 A1 | 11/2012 | Mon et al. |
| 2013/0006139 A1 | 1/2013 | Tiano |
| 2013/0006238 A1 | 1/2013 | Ditter et al. |
| 2013/0030385 A1 | 1/2013 | Schultz et al. |
| 2013/0030426 A1 | 1/2013 | Gallardo et al. |
| 2013/0030427 A1 | 1/2013 | Betts et al. |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079768 A1 | 3/2013 | De Luca et al. |
| 2013/0096447 A1 | 4/2013 | Dhawan et al. |
| 2013/0110104 A1 | 5/2013 | Corvi et al. |
| 2013/0123775 A1 | 5/2013 | Grunewald et al. |
| 2013/0137999 A1 | 5/2013 | Wenzel et al. |
| 2013/0158536 A1 | 6/2013 | Bloom |
| 2013/0172742 A1 | 7/2013 | Rankin et al. |
| 2013/0172873 A1 | 7/2013 | Govari et al. |
| 2013/0172879 A1 | 7/2013 | Sutermeister et al. |
| 2013/0184549 A1 | 7/2013 | Avitall et al. |
| 2013/0190747 A1 | 7/2013 | Koblish et al. |
| 2013/0197504 A1 | 8/2013 | Cronin et al. |
| 2013/0197507 A1 | 8/2013 | Kim et al. |
| 2013/0204124 A1 | 8/2013 | Duindam et al. |
| 2013/0204240 A1 | 8/2013 | McCarthy et al. |
| 2013/0226169 A1 | 8/2013 | Miller et al. |
| 2013/0237977 A1 | 9/2013 | McCarthy et al. |
| 2013/0237979 A1 | 9/2013 | Shikhman et al. |
| 2013/0253504 A1 | 9/2013 | Fang |
| 2013/0253505 A1 | 9/2013 | Schultz |
| 2013/0272339 A1 | 10/2013 | Tofighi |
| 2013/0281851 A1 | 10/2013 | Carr et al. |
| 2013/0289550 A1 | 10/2013 | Ingle et al. |
| 2013/0303892 A1 | 11/2013 | Zhao et al. |
| 2013/0303945 A1 | 11/2013 | Blumenkranz et al. |
| 2013/0310674 A1 | 11/2013 | Deno et al. |
| 2013/0324993 A1 | 12/2013 | McCarthy et al. |

(56) References Cited

U.S. PATENT DOCUMENTS

| | | |
|---|---|---|
| 2013/0345692 A1 | 12/2013 | Brannan |
| 2014/0012132 A1 | 1/2014 | Carr et al. |
| 2014/0018697 A1 | 1/2014 | Allison |
| 2014/0018793 A1 | 1/2014 | Sharonov |
| 2014/0025056 A1 | 1/2014 | Dowlatshahi |
| 2014/0025057 A1 | 1/2014 | Hoey et al. |
| 2014/0051959 A1 | 2/2014 | Gliner et al. |
| 2014/0058244 A1 | 2/2014 | Krocak |
| 2014/0058375 A1 | 2/2014 | Koblish |
| 2014/0081111 A1 | 3/2014 | Tun et al. |
| 2014/0081112 A1 | 3/2014 | Kim et al. |
| 2014/0081262 A1 | 3/2014 | Koblish et al. |
| 2014/0094794 A1 | 4/2014 | Orszulak |
| 2014/0142561 A1 | 5/2014 | Reu et al. |
| 2014/0171821 A1 | 6/2014 | Govari et al. |
| 2014/0171936 A1 | 6/2014 | Govari et al. |
| 2014/0180077 A1 | 6/2014 | Huennekens et al. |
| 2014/0187949 A1 | 7/2014 | Zhao et al. |
| 2014/0188440 A1 | 7/2014 | Donhowe et al. |
| 2014/0194867 A1 | 7/2014 | Fish et al. |
| 2014/0207010 A1 | 7/2014 | Schecter |
| 2014/0214017 A1 | 7/2014 | Brannan |
| 2014/0214110 A1 | 7/2014 | Yang et al. |
| 2014/0243813 A1 | 8/2014 | Paul et al. |
| 2014/0249510 A1 | 9/2014 | Koblish et al. |
| 2014/0249521 A1 | 9/2014 | McCarthy et al. |
| 2014/0257261 A1 | 9/2014 | Kim et al. |
| 2014/0276716 A1 | 9/2014 | Melsheimer |
| 2014/0276755 A1 | 9/2014 | Cao et al. |
| 2014/0276811 A1 | 9/2014 | Koblish et al. |
| 2014/0288548 A1 | 9/2014 | Kim et al. |
| 2014/0336638 A1 | 11/2014 | Deem et al. |
| 2014/0343416 A1 | 11/2014 | Panescu et al. |
| 2014/0378956 A1 | 12/2014 | Shafirstein |
| 2015/0011995 A1 | 1/2015 | Avitall et al. |
| 2015/0105645 A1 | 4/2015 | Subramaniam et al. |
| 2015/0105765 A1 | 4/2015 | Panescu et al. |
| 2015/0133914 A1 | 5/2015 | Koblish |
| 2015/0133920 A1 | 5/2015 | Rankin et al. |
| 2015/0342676 A1 | 12/2015 | McCarthy et al. |
| 2016/0038229 A1 | 2/2016 | McCarthy et al. |
| 2016/0199131 A1 | 7/2016 | Allison et al. |

FOREIGN PATENT DOCUMENTS

| | | |
|---|---|---|
| EP | 2008602 | 12/2008 |
| EP | 1803407 | 11/2010 |
| EP | 2294490 | 3/2011 |
| EP | 1962710 | 8/2015 |
| EP | 1962708 | 9/2015 |
| JP | H06-503028 | 4/1994 |
| JP | H06-510450 | 11/1994 |
| JP | T-2002-523127 | 7/2002 |
| JP | 2003-52736 | 2/2003 |
| JP | T-2004-500935 | 1/2004 |
| JP | T-2006-500103 | 1/2006 |
| WO | WO 1993/02747 | 2/1993 |
| WO | WO 1993/04727 | 3/1993 |
| WO | WO 1999/003535 | 1/1999 |
| WO | WO 1999/044523 | 9/1999 |
| WO | WO 2000/010472 | 3/2000 |
| WO | WO 2000/036987 | 6/2000 |
| WO | WO 2001/098764 | 12/2001 |
| WO | WO 2003/028572 | 4/2003 |
| WO | WO 2003/047446 | 6/2003 |
| WO | WO 2003/070298 | 8/2003 |
| WO | WO 2004/026098 | 4/2004 |
| WO | WO 2004/073505 | 9/2004 |
| WO | WO 2004/084748 | 10/2004 |
| WO | WO 2004/107974 | 12/2004 |
| WO | WO 2005/007000 | 1/2005 |
| WO | WO 2006/074571 | 7/2006 |
| WO | WO 2007/019876 | 2/2007 |
| WO | WO 2008/002517 | 1/2008 |
| WO | WO 2010/090701 | 8/2010 |
| WO | WO 2012/120498 | 9/2012 |
| WO | WO 2013/009977 | 1/2013 |
| WO | WO 2013/019544 | 2/2013 |
| WO | WO 2013/034629 | 3/2013 |
| WO | WO 2013/119620 | 8/2013 |
| WO | WO 2013/123020 | 8/2013 |
| WO | WO 2013/138262 | 9/2013 |
| WO | WO 2014/097300 | 6/2014 |
| WO | WO 2015/033317 | 3/2015 |
| WO | WO 2015/042173 | 3/2015 |
| WO | WO 2015/104672 | 7/2015 |
| WO | WO 2015/200518 | 12/2015 |
| WO | WO 2016/081598 | 5/2016 |
| WO | WO 2016/081602 | 5/2016 |
| WO | WO 2016/081606 | 5/2016 |
| WO | WO 2016/081611 | 5/2016 |
| WO | WO 2016/081650 | 5/2016 |

OTHER PUBLICATIONS

Arunachalam et al., "Characterization of a digital microwave radiometry system for noninvasive thermometry using temperature controlled homogeneous test load," Phys. Med. Biol. 53(14): 3883-3901, Jul. 21, 2008.

Calkins, "Breaking News! When It Comes to Complications of Catheter Ablation of Atrial Fibrillation, Experience Matters," Circulation, 2013; 128: 2099-2100 (Sep. 2013).

Carr, "Thermography: Radiometric sensing in medicine," New Frontiers in Medical Device Technology, Edited by Rosen et al., pp. 311-342, 1995.

Chierchia et al., "An Initial Clinical Experience with a Novel Microwave Radiometry Sensing Technology used in Irrigated RF Ablation for Flutter" (datE:Jan. 1, 2011).

ConstellationTM, Full Contact Mapping Catheter, Boston Scientific Corporation Brochure, Dec. 2014.

El-Sharkawy et al., "Absolute temperature monitoring using RF radiometry in the MRI scanner," IEEE Trans Circuits Syst I Regul Pap. 53(11): 2396-2404, Nov. 2006.

Ikeda et al., "Microwave Volumetric Temperature Sensor Improves Control of Radiofrequency Lesion Formation and Steam Pop," Presentation Abstract, May 2012.

Ikeda et al., "Novel Irrigated Radiofrequency Ablation Catheter With Microwave Volumetric Temperature Sensor Predicts Lesion Size and Incidence of Steam Pop in Canine Beating Heart," Presentation Abstract, May 2012.

Jacobsen et al., "Dual-mode antenna design for microwave heating and noninvasive thermometry of superficial tissue disease," IEEE Transactions on Biomedical Engineering 47(11): 1500-1509, Nov. 2000.

Johnson et al., "Automatic Temperature Controller for Multielement Array Hyperthermia Systems", IEEE Transactions on Biomedical Engeineering, vol. 53, No. 6, 1006-1015, Jun. 2016.

Koruth et al., "Occurrence of Steam Pops During Irrigated RF Ablation: Novel Insights from Microwave Radiometry," J. Cardiovasc. Electrophysiol., vol. 24, Issue 11, pp. 1271-1277, Nov. 2013.

Koruth et al., "Tissue Temperature Sensing During Irrigated Radiofrequency Ablation: A Novel Strategy to Predict Steam Pops," Presentation Abstract, May 2012.

Lantis et al, "Microwave Applications in Clinical Medicine," Surgical Endoscopy, vol. 12, Issue 2, pp. 170-176, Feb. 1998.

Panescu et al., Three-Dimensional Finite Element Analysis of Current Density and Temperature Distributions During Radio-Frequency Ablation, IEEE Transactions on Biomedical Engineering (1995) 42(9):879-889.

Schecter et al., "Palpation of Intra-cardiac Blood Flow, Pressure, Contact Force and Motor Reaction Time of Subjects Using a Novel Haptic Feedback System", Poster Contributions, JACC vol. 65, Issue 10S, Mar. 17, 2015.

Schecter et al., "Tactile Feedback Provides Real Time In Vivo TissuE:Catheter Contact Force Information During Cardiac Radiofrequency Ablation"—Abstract, Journal of Cardiovascular Electrophysiology, vol. 27, No. 5, p. 649, May 2016.

(56) References Cited

OTHER PUBLICATIONS

Stevenson, "Irrigated RF ablation: Power titration and fluid management for optimal safety and efficacy," Biosense Webster, Inc., 4 pages, 2005.

Tokmakoff et al, "Thermal Diffusivity Measurements of Natural and Isotopically Enriched Diamond by Picosecond Infrared Transient Grating Experiments," Appl. Phys., A56, pp. 87-90 (1993).

Tungjitkusolmun et al., "Finite element analyses of uniform current density electrodes for radio-frequency cardiac ablation," in IEEE Transactions on Biomedical Engineering, vol. 47, No. 1, pp. 32-40, Jan. 2000.

Tungjitkusolmun et al., "Three-dimensional finite-element analyses for radio-frequency hepatic tumor ablation," in IEEE Transactions on Biomedical Engineering, vol. 49, No. 1, pp. 3-9, Jan. 2002.

Vandekerckhove et al., "Flutter Ablation with an Irrigated Catheter Using Microwave Radiometry Sensing Technology: first report in men" (datE:Jan. 1, 2011).

Wang et al., "Microwave Radiometric Thermometry and its Potential Applicability to Ablative Therapy," Journal of Interventional Cardiac Electrophysiology, vol. 4, pp. 295-300, Apr. 2000.

Wang et al., "Tissue Dielectric Measurement Using an Interstitial Dipole Antenna," IEEE Trans Biomed. Eng., vol. 59, No. 1, 115-121, Jan. 2012.

Yazdandoost et al., "Theoretical study of the power distributions for interstitial microwave hyperthermia," Proceedings of the 2002 WSEAS International Conferences, Cadiz, Spain, pp. 1021-1025, Jun. 12-16, 2002.

\* cited by examiner

METHODS AND SYSTEMS FOR ENHANCED MAPPING OF TISSUE

RELATED APPLICATIONS

This application is a continuation of U.S. patent application Ser. No. 15/179,891, filed Jun. 10, 2016, which is a continuation application of PCT/US2015/061353, filed Nov. 18, 2015, which claims priority to U.S. Provisional Application No. 62/081,710, filed Nov. 19, 2014, and U.S. Provisional Application No. 62/159,898, filed May 11, 2015, the entire contents of each of which are incorporated herein by reference in their entirety.

BACKGROUND

Tissue ablation may be used to treat a variety of clinical disorders. For example, tissue ablation may be used to treat cardiac arrhythmias by at least partially destroying (e.g., at least partially or completely ablating, interrupting, inhibiting, terminating conduction of, otherwise affecting, etc.) aberrant pathways that would otherwise conduct abnormal electrical signals to the heart muscle. Several ablation techniques have been developed, including cryoablation, microwave ablation, radio frequency (RF) ablation, and high frequency ultrasound ablation. For cardiac applications, such techniques are typically performed by a clinician who introduces a catheter having an ablative tip to the endocardium via the venous vasculature, positions the ablative tip adjacent to what the clinician believes to be an appropriate region of the endocardium based on tactile feedback, mapping electrocardiogram (ECG) signals, anatomy, and/or fluoroscopic imaging, actuates flow of an irrigant to cool the surface of the selected region, and then actuates the ablative tip for a period of time and at a power believed sufficient to destroy tissue in the selected region.

Successful electrophysiology procedures require precise knowledge about the anatomic substrate. Additionally, ablation procedures may be evaluated within a short period of time after their completion. Cardiac ablation catheters typically carry only regular mapping electrodes. Cardiac ablation catheters may incorporate high-resolution mapping electrodes. Such high-resolution mapping electrodes provide more accurate and more detailed information about the anatomic substrate and about the outcome of ablation procedures.

SUMMARY

According to some embodiments, a device for high-resolution mapping and ablating targeted tissue of subject comprises an elongate body (e.g., a catheter, another medical instrument, etc.) having a proximal end and a distal end, a first high-resolution electrode portion positioned on the elongate body, at least a second electrode portion positioned adjacent the first electrode portion, the first and second electrode portions being configured to contact tissue of a subject and deliver radiofrequency energy sufficient to at least partially ablate the tissue, and at least one electrically insulating gap positioned between the first electrode portion and the second electrode portion, the at least one electrically insulating gap comprising a gap width separating the first and second electrode portions, wherein the first electrode portion is configured to electrically couple to the second electrode portion using a filtering element, wherein the filtering element is configured to present a low impedance at a frequency used for delivering ablative energy via the first and second electrode portions, wherein the device is configured to be positioned within targeted tissue of the subject to obtain high-resolution mapping data related to said tissue when ablative energy is not delivered to the first and second electrode portions, wherein, based in part of the obtained mapping data, the device is configured to ablate one or more regions of the subject's targeted tissue once ablative energy is delivered to the first and said electrode portions, and wherein the device is used as a roving device in conjunction with a separate mapping device or system to provide mapping data in tissue regions not adequately covered by said separate mapping system, wherein the separate mapping device or system comprises a plurality of mapping electrodes.

According to some embodiments, the device additionally includes at least one separator positioned within the at least one electrically insulating gap, wherein the elongate body comprises at least one irrigation passage, said at least one irrigation passage extending to the first electrode portion, wherein electrically separating the first and second electrode portions facilitates high-resolution mapping along a targeted anatomical area, wherein the filtering element comprises a capacitor, wherein the device comprises the filtering element, wherein the filtering element, wherein the filtering element is included on or within the elongate body, wherein the mapping electrodes of the separate mapping device or system are unipolar or bipolar electrodes, and wherein the separate mapping device or system comprises a plurality of mapping electrodes.

According to some embodiments, electrically separating the first and second electrode portions facilitates high-resolution mapping along a targeted anatomical area, and the separate mapping device or system comprises a plurality of mapping electrodes (e.g., a multi-electrode mapping system).

According to some embodiments, the device is used as a roving device in conjunction with a separate mapping device or system to provide mapping data in tissue regions not adequately covered by said separate mapping system. In some embodiments, the separate mapping device or system comprises a plurality of mapping electrodes (e.g., unipolar or bipolar electrodes). In some embodiments, the device comprises the filtering element. In one embodiment, the filtering element is separate from the device. In some embodiments, the filtering element is included on or within the elongate body. In some embodiments, the filtering element is included on or within a proximal handle secured to the elongate body. In several arrangements, the filtering element is included on or within a generator configured to supply power to the first high-resolution electrode portion and the at least a second electrode portion.

According to some embodiments, the device additionally comprises a means for facilitating high-resolution mapping. In some embodiments, electrically separating the first and second electrode portions facilitates high-resolution mapping along a targeted anatomical area.

According to some embodiments, the device further includes at least one separator positioned within the at least one electrically insulating gap. In one embodiment, the at least one separator contacts a proximal end of the first electrode portion and the distal end of the second electrode portion. In some embodiments, the filtering element comprises a capacitor. In some embodiments, the capacitor comprises a capacitance of 50 to 300 nF (e.g., approximately 100 nF, 50-75, 75-100, 100-150, 150-200, 200-250, 250-300 nF, ranges between the foregoing, etc.). In one embodiment, the capacitor comprises a capacitance of 100 nF. In some arrangements, a series impedance of lower than about 3 ohms (Ω) is introduced across the first and second electrodes in the operating RF frequency range. In some embodiments, the operating RF frequency range is 300 kHz to 10 MHz. In some embodiments, the filtering element comprises a LC circuit.

According to some embodiments, the device additionally includes at least one conductor configured to electrically couple an energy delivery module to at least one of the first and second electrode portions. In one embodiment, the at least one conductor is electrically coupled to an energy delivery module.

According to some embodiments, a frequency of energy provided to the first and second electrode portions is in the radiofrequency range. In some embodiments, a series impedance introduced across the first and second electrode portions is lower than: (i) an impedance of a conductor that electrically couples the electrodes to an energy delivery module, and (ii) an impedance of a tissue being treated. In some embodiments, the gap width is approximately 0.2 to 1.0 mm (e.g., 0.2-0.3, 0.3-0.4, 0.4-0.5, 0.5-0.6, 0.6-0.7, 0.7-0.8, 0.8-0.9, 0.9-1 mm, lengths between the foregoing ranges, etc.). In one embodiment, the gap width is 0.5 mm. In some embodiments, the gap width is approximately 0.2 to 1.0 mm (e.g., 0.2-0.3, 0.3-0.4, 0.4-0.5, 0.5-0.6, 0.6-0.7, 0.7-0.8, 0.8-0.9, 0.9-1.0 mm, widths between the foregoing, etc.).

According to some embodiments, the elongate body comprises at least one irrigation passage, the at least one irrigation passage extending to the first electrode portion. In some embodiments, the first electrode comprises at least one outlet port in fluid communication with the at least one irrigation passage. In one embodiment, the mapping electrodes of the separate mapping device or system are unipolar or bipolar electrodes.

According to some embodiments, the device is configured to determine whether tissue has been properly ablated. In some embodiments, a determination of whether tissue has been properly ablated is determined by comparing the amplitude of an electrogram obtained using the first and second electrode portions to a baseline electrogram amplitude.

According to some embodiments, a method of mapping targeted anatomical tissue of a subject and delivering energy to at least an area of said anatomical tissue comprises positioning a high-resolution tip or high-resolution section electrode located on a catheter, the high-resolution tip or high-resolution section electrode comprising a first electrode portion and a second electrode portion, wherein an electrically insulating gap is positioned between the first electrode portion and the second electrode portion, the electrically insulating gap comprising a gap width separating the first and second electrode portions, wherein a filtering element electrically couples the first electrode to the second electrode portion, and wherein electrically separating the first and second electrode portions facilitates high-resolution mapping along a targeted anatomical area According to some embodiments, the catheter comprises the filtering element. In some embodiments, the filtering element is separate from the catheter. In some embodiments, the method further includes receiving high-resolution mapping data from the first and second electrode portions, the high-resolution mapping data relating to tissue of a subject adjacent the first and second electrode portions. In some embodiments, the high-resolution-tip or high-resolution-section electrode is positioned in regions of a subject's tissue not mapped by a separate mapping device or system. In some embodiments, the high-resolution-tip or high-resolution-section electrode is positioned without the use or assistance of a separate mapping device or system.

According to some embodiments, the first and second electrode portions are configured to contact tissue of a subject and selectively deliver energy sufficient to at least partially ablate tissue. In some embodiments, selectively delivering energy sufficient to at least partially ablate tissue is based, at least in part, of the high-resolution mapping of the targeted anatomical area obtained by the high-resolution tip or high-resolution section electrode located on the catheter. In one embodiment, receiving high-resolution mapping data occurs prior to, during or after energizing a high-resolution tip electrode positioned on a catheter.

According to some embodiments, the method additionally includes comprising determining whether tissue being mapped has been properly ablated. In some embodiments, determining whether tissue has been properly ablated comprises comparing the amplitude of an electrogram obtained using the first and second electrode portions to a baseline electrogram amplitude.

According to some embodiments, a method of mapping tissue of a subject comprises receiving high-resolution mapping data using a high-resolution-tip or high-resolution-section electrode, said high-resolution-tip or high-resolution-section electrode comprising first and second electrode portions, wherein the high-resolution-tip or high-resolution-section electrode comprises a first electrode portion and a second electrode portion separated by an electrically insulating gap, wherein a filtering element electrically couples the first electrode portion to the second electrode portion in the operating RF range, and wherein electrically insulating the first and second electrode portions facilitates high-resolution mapping along a targeted anatomical area.

According to some embodiments, the filtering element is positioned adjacent the high-resolution-tip or the high-resolution-section electrode. In some embodiments, the filtering element is separate or away from the high-resolution-tip or the high-resolution-section electrode. In some embodiments, the method further comprises energizing the high-resolution-tip or high-resolution-section electrode to selectively deliver energy sufficient to at least partially ablate the tissue of the subject.

According to some embodiments, the high-resolution mapping data relates to tissue of a subject adjacent the first and second electrode portions. In some embodiments, receiving high-resolution mapping data occurs prior to, during or after energizing a high-resolution tip or a high-resolution section electrode positioned on a catheter. In one embodiment, the mapping data is provided to an electrophysiology recorder.

According to some embodiments, a frequency of energy provided to the first and second electrodes is in the radiofrequency range. In some embodiments, the filtering element comprises a capacitor. In some embodiments, the capacitor comprises a capacitance of 50 to 300 nF (e.g., approximately 100 nF, 50-75, 75-100, 100-150, 150-200, 200-250, 250-300 nF, etc.). In one embodiment, the capacitor comprises a capacitance of 100 nF. In some arrangements, a series impedance of lower than about 3 ohms (Ω) is introduced across the first and second electrodes in the operating RF frequency range. In some embodiments, the operating RF frequency range is 300 kHz to 10 MHz. In some embodiments, the filtering element comprises a LC circuit.

According to some embodiments, a device on which the high-resolution-tip or high-resolution-section electrode is positioned is used as a roving device in conjunction with a separate mapping device or system to provide mapping data in tissue regions not adequately covered by said separate mapping device or system. In some embodiments, the separate mapping device or system comprises a plurality of mapping electrodes. In some embodiments, the mapping electrodes of the separate mapping device or system are unipolar or bipolar electrodes.

According to some embodiments, a device on which the high-resolution-tip or high-resolution-section electrode is positioned is configured to determine whether tissue has been properly ablated. In some embodiments, a determination of whether tissue has been properly ablated is determined by comparing the amplitude of an electrogram obtained using the first and second electrode portions to a baseline electrogram amplitude.

According to some embodiments, a system for obtaining mapping data for a targeted anatomical tissue of a subject comprises a data acquisition device configured to receive mapping data from a first device, the first device comprising at least one high-resolution electrode configured to map tissue along the targeted anatomical tissue, wherein the data acquisition device is further configured to receive mapping data from a second device, the second device comprising a plurality of mapping electrodes, and a processor configured to generate a three-dimensional map using the mapping data received by the data acquisition device from the first and second devices.

According to some embodiments, the first device comprises a catheter. In one embodiment, the catheter comprises a high-resolution-tip electrode. In some embodiments, the second device comprises at least one expandable member, wherein at least some of the plurality of mapping electrodes are positioned along the at least one expandable member. In some embodiments, the mapping data received from the second device comprise unipolar signals. In some embodiments, the mapping data received from the second device comprise bipolar signals.

According to some embodiments, the processor is configured to align or synchronize data obtained from the first and second devices. In some embodiments, the processor is configured to couple to an output device for displaying the three-dimensional map. In one embodiment, the system comprises the output device (e.g., monitor).

According to some embodiments, the system further comprises the first device and/or the second devices. In some embodiments, the data acquisition device and the processor are combined in a single assembly. In other arrangements, the data acquisition device and the processor are separate.

According to some embodiments, a system for obtaining mapping data for a targeted anatomical tissue of a subject comprises a catheter including at least one high-resolution electrode configured to map tissue along the targeted anatomical tissue, and a data acquisition device configured to receive mapping data from the catheter, wherein the data acquisition device is configured to couple to a separate mapping device, the data acquisition device being configured to receive mapping data from the separate mapping device, wherein the separate mapping device comprises a plurality of mapping electrodes. The system additionally includes a processor configured to generate a three-dimensional map from the mapping data received from the catheter and the separate mapping device by the data acquisition device.

According to some embodiments, the catheter comprises a high-resolution-tip electrode. In some embodiments, the separate mapping system comprises at least one expandable member, wherein at least some of the plurality of mapping electrodes are positioned along the at least one expandable member. In some embodiments, the mapping data received from the separate mapping device comprise unipolar signals. In some embodiments, the mapping data received from the separate mapping device comprise bipolar signals. In some embodiments, the processor is configured to align or synchronize mapping data obtained from the catheter and the separate mapping device. In some embodiments, the processor is configured to couple to an output device for displaying the three-dimensional map. In one embodiment, the system comprises the output device (e.g., one or more monitors). In some embodiments, the processor is integrated within the data acquisition device. In other embodiments, the processor is separate from the data acquisition device.

According to some embodiments, a system for obtaining mapping data for a targeted anatomical tissue of a subject comprises a data acquisition device configured to receive mapping data from a mapping catheter, and a processor configured to receive mapping data from the data acquisition device and from a separate mapping system, wherein the separate mapping system is configured to operatively couple to the processor, the separate mapping system comprising a plurality of mapping electrodes, and wherein the processor is configured to generate a three-dimensional map from such mapping data.

According to some embodiments, the system if configured to operatively couple to an output device for displaying said three-dimensional map. In some embodiments, the system further includes the output device (e.g., one or more monitors or other displays). In some embodiments, the at least one electrode of the catheter comprises a high-resolution-tip electrode. In some embodiments, the at least one electrode of the catheter comprises a bipolar electrode.

According to some embodiments, the separate mapping device comprises at least one expandable member (e.g., strut, wire, cage, etc.), the at least one expandable member comprising at least one of the plurality of mapping electrodes. In some embodiments, the separate mapping device comprises an expandable basket or other expandable structure. In some embodiments, at least one of the mapping electrodes of the separate mapping device comprises a bipolar electrode. In some embodiments, at least one of the mapping electrodes of the separate mapping device comprises a unipolar electrode. In some embodiments, the separate mapping device is configured to work with at least one reference electrode in order to generate the mapping data for the separate mapping device. In one embodiment, the at least one reference electrode is located external to the subject. In some embodiments, the at least one reference electrode is located internal to the subject. In some embodiments, the at least one reference electrode is located within a lumen of a subject. In some embodiments, the lumen of the subject comprises a superior vena cava of the subject.

According to some embodiments, the processor is configured to align or synchronize data obtained from the catheter and from the separate device. In some embodiments, the system further comprises a user input device (e.g., touchscreen, other keyboard or keypad, a computer, etc.) that allows a user to input information or data. In some embodiments, the processor is configured to operatively couple to a user input device, the user input device allowing a user to input information or data. In one embodiment, the user input device is incorporated into the output device. In some embodiments, the user input device is separate from the output device.

According to some embodiments, the at least one high-resolution electrode comprises a first high-resolution electrode portion. In some embodiments, the processor is integrated within the data acquisition device. In some embodiments, the processor is separate from the data acquisition device.

According to some embodiments, the system further includes the catheter. In some embodiments, the catheter comprises at least one high-resolution electrode configured to map tissue along the targeted anatomical tissue. In some embodiments, the separate mapping system comprises a separate data acquisition device, the separate data acquisition device being configured to receive data from the plurality of mapping electrodes of said separate mapping system. In one embodiment, the separate data acquisition system is configured to operatively couple to the processor.

According to some embodiments, a method of enhancing a map of a targeted anatomical region includes receiving mapping data from a first mapping device or system, the first mapping device or system comprising a plurality of mapping electrodes, receiving high-resolution mapping data from a second mapping system, the second mapping system being configured to be moved to locations between the plurality of mapping electrodes of the first mapping system to obtain said high-resolution mapping data, wherein the second mapping device or system comprises a roving system that can be selectively positioned along a targeted anatomical region of a subject, processing the mapping data obtained by the first and second mapping devices or systems using a processor, wherein the second mapping device or system is configured to supplement and refine a map of the targeted anatomical region, and creating an enhanced three-dimensional map using the processor with the data obtained by the first and second mapping devices or systems.

According to some embodiments, the method further comprises displaying the three-dimensional map (e.g., on a monitor or other display). In some embodiments, the method further comprises aligning or synchronizing the data obtained from the plurality of mapping electrodes of the first mapping device or system and from the high-resolution roving device or system. In some embodiments, the high-resolution mapping data is obtained using a high-resolution electrode of the second mapping device or system. In some embodiments, the data from the plurality of mapping electrodes comprise unipolar signals. In some embodiments, the data from the plurality of mapping electrodes comprise bipolar signals.

According to some embodiments, the first mapping device or system comprises at least one expandable member, wherein at least some of the mapping electrodes are located on the at least one expandable member. In some embodiments, the targeted anatomical region is located along or near the heart of a subject. In some embodiments, the targeted anatomical region comprises cardiac tissue. In some embodiments, the three-dimensional map comprising at least one of an activation map, a propagation velocity map, a voltage map and a rotor map.

According to some embodiments, a method of creating an enhanced map of a targeted anatomical region includes collecting a first mapping data set from a plurality of mapping electrodes, collecting a second mapping data set from a high-resolution roving electrode being configured to be moved to locations between the plurality of mapping electrodes, aligning or synchronizing the first and second mapping data sets, and generating an enhanced three-dimensional map using the aligned or synchronized first and second mapping data sets.

According to some embodiments, the method further includes displaying the enhanced three-dimensional map. In one embodiment, data related to the enhanced three-dimensional map are provided to an output device (e.g., monitor or other display) for displaying the three-dimensional map. In some embodiments, the data from the plurality of mapping electrodes comprise unipolar signals. In some embodiments, the data from the plurality of mapping electrodes of the first mapping system comprise bipolar signals.

According to some embodiments, the plurality of mapping electrodes are part of a multi-electrode mapping device or system, the multi-electrode device or system comprising at least one expandable member, wherein at least some of the mapping electrodes are located on the at least one expandable member. In some embodiments, the roving system comprises a catheter, the catheter comprising at least one mapping electrode. In one embodiment, the targeted anatomical region is located along or near the heart of a subject. In some embodiments, the targeted anatomical region comprises cardiac tissue. In some embodiments, the three-dimensional map comprising at least one of an activation map, a propagation velocity map, a voltage map and a rotor map. In some embodiments, According to some embodiments, a kit for obtaining mapping data of tissue comprises a device for high-resolution mapping in accordance with any one of the device configurations disclosed herein, and a separate mapping device or system, wherein the separate mapping device or system comprises a plurality of mapping electrodes configured to map tissue of a subject, and wherein the device for high-resolution mapping provides mapping data in tissue regions not adequately covered by the separate mapping device or system.

According to some embodiments, a kit for obtaining mapping data of tissue comprises a device for high-resolution mapping, the device including an elongate body comprising a proximal end and a distal end, a first high-resolution electrode portion positioned on the elongate body, at least a second electrode portion positioned adjacent the first electrode portion, the first and second electrode portions being configured to contact tissue of a subject, and at least one electrically insulating gap positioned between the first electrode portion and the second electrode portion, the at least one electrically insulating gap comprising a gap width separating the first and second electrode portions, wherein the first electrode portion is configured to electrically couple to the second electrode portion using a filtering element, wherein the filtering element is configured to present a low impedance at a frequency used for delivering ablative energy via the first and second electrode portions, wherein the device is configured to be positioned within targeted tissue of the subject to obtain high-resolution mapping data related to said tissue when ablative energy is not delivered to the first and second electrode portions. The kit further comprising a separate mapping device or system, wherein the separate mapping device or system comprises a plurality of mapping electrodes configured to map tissue of a subject, and wherein the device for high-resolution mapping provides mapping data in tissue regions not adequately covered by the separate mapping device or system.

According to some embodiments, the kit further includes a data acquisition device configured to receive mapping data from the device, wherein the data acquisition device is further configured to receive mapping data from the separate mapping device or system. In some embodiments, the kit additionally comprises a processor configured to generate a three-dimensional map using the mapping data received by the data acquisition device from the device and from the separate mapping device or system. In some embodiments, the separate mapping device or system comprises at least one expandable member, wherein at least some of the plurality of mapping electrodes are positioned along the at least one expandable member.

According to some embodiments, the mapping data received from the separate mapping device or system comprise unipolar signals. In some embodiments, the mapping data received from the separate mapping device or system comprise bipolar signals. In some embodiments, the processor is configured to align or synchronize data obtained from the device and the separate mapping device or system. In some embodiments, the processor is configured to couple to an output device for displaying the three-dimensional map.

According to some embodiments, a processor for receiving and processing data received from separate mapping devices or systems comprises a first port configured to operatively connect to a first device for high-resolution mapping, the device comprising a catheter and an electrode assembly for receiving high-resolution mapping data, and a second port configured to operatively connect to a second mapping device or system, the second mapping device or system comprising a plurality of electrodes that are configured to contact various portions along a targeted region of tissue being mapped, wherein the processor is configured to combine mapping data obtained from the first device and from the second mapping device or system, and wherein the processor is configured to align the mapping data received from the first device and the second mapping device or system to enable for the generation of a more complete three-dimensional map of tissue being mapped. In some embodiments, the processor is configured to be operatively coupled to an output device (e.g., at least one monitor or other display) for displaying the three-dimensional map created from data of both the first device and the second device or system.

According to some embodiments, a generator for selectively delivering energy to an ablation device comprises a processor according to any one of the embodiments disclosed herein, and an energy delivery module configured to generate ablative energy for delivery to an ablation device, wherein ablative energy generated by the energy delivery module is delivered to and through the first device to the electrode assembly of the first device. In some embodiments, the energy delivery module is configured to generated radiofrequency (RF) energy. In some embodiments, the processor and the energy delivery module are located within a single housing or enclosure. In some embodiments, the processor and the energy delivery module are located within separate housings or enclosures.

BRIEF DESCRIPTION OF THE DRAWINGS

These and other features, aspects and advantages of the present application are described with reference to drawings of certain embodiments, which are intended to illustrate, but not to limit, the concepts disclosed herein. The attached drawings are provided for the purpose of illustrating concepts of at least some of the embodiments disclosed herein and may not be to scale.

DETAILED DESCRIPTION

According to some embodiments, successful electrophysiology procedures require precise knowledge about the anatomic substrate being targeted. Additionally, it may be desirable to evaluate the outcome of an ablation procedure within a short period of time after the execution of the procedure (e.g., to confirm that the desired clinical outcome was achieved). Typically, ablation catheters include only regular mapping electrodes (e.g., ECG electrodes). However, in some embodiments, it may be desirable for such catheters to incorporate high-resolution mapping capabilities. In some arrangements, high-resolution mapping electrodes can provide more accurate and more detailed information about the anatomic substrate and about the outcome of ablation procedures. For example, such high-resolution mapping electrodes can allow the electrophysiology (EP) practitioner to evaluate the morphology of electrograms, their amplitude and width and/or to determine changes in pacing thresholds. According to some arrangements, morphology, amplitude and/or pacing threshold are accepted as reliable EP markers that provide useful information about the outcome of ablation.

Several embodiments disclosed herein are particularly advantageous because they include one, several or all of the following benefits or advantages: reducing proximal edge heating, reducing the likelihood of char formation, providing for feedback that may be used to adjust ablation procedures in real time, providing noninvasive temperature measurements, providing for the creation of a more complete and comprehensive map (e.g., three-dimensional map) of tissue being evaluated, providing for more targeted ablation of tissue to treat a condition (e.g., atrial fibrillation, other cardiac arrhythmias, etc.) based on the more complete map of tissue, providing for integration (e.g., seamless or near seamless integration) with a separate mapping system, providing safer and more reliable ablation procedures and/or the like.

According to some embodiments, various implementations of electrodes (e.g., radiofrequency or RF electrodes) that can be used for high-resolution mapping are disclosed herein. For example, as discussed in greater detail herein, an ablation or other energy delivery system can comprise a high-resolution-tip design, wherein the energy delivery member (e.g., radiofrequency electrode) comprises two or more separate electrodes or electrode portions. As also discussed herein, in some embodiments, such separate electrodes or electrode portions can be advantageously electrically coupled to each other (e.g., to collectively create the desired heating or ablation of targeted tissue).

Figure 1:
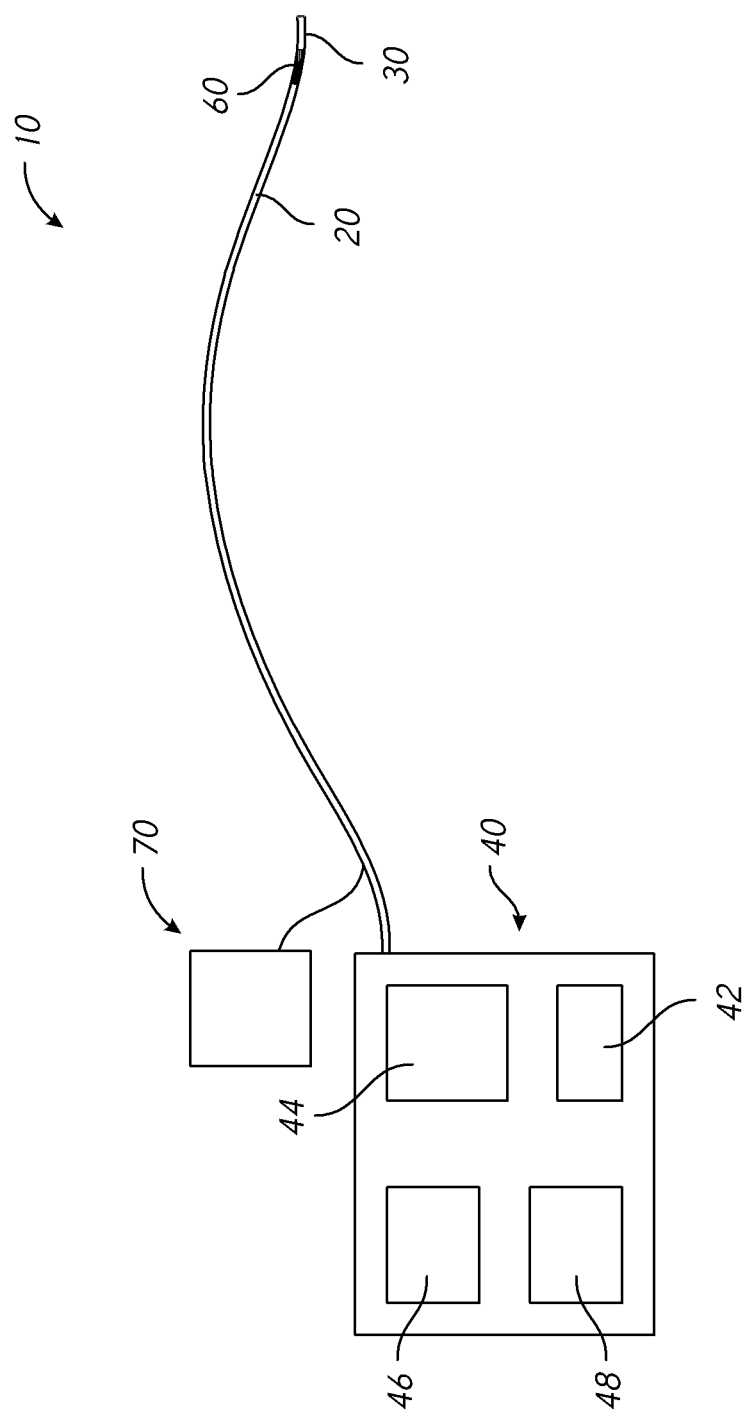
FIG. 1 schematically illustrates one embodiment of an energy delivery system configured to selectively ablate or otherwise heat targeted tissue of a subject.

FIG. 1 schematically illustrates one embodiment of an energy delivery system 10 that is configured to selectively ablate, stimulate, modulate and/or otherwise heat or treat targeted tissue (e.g., cardiac tissue, pulmonary vein, other vessels or organs, etc.). Although certain embodiments disclosed herein are described with reference to ablation systems and methods, any of the systems and methods can be used to stimulate, modulate, heat and/or otherwise affect tissue, with or without partial or complete ablation, as desired or required. As shown, the system 10 can include a medical instrument 20 (e.g., catheter) comprising one or more energy delivery members 30 (e.g., radiofrequency electrodes) along a distal end of the medical instrument 20. The medical instrument can be sized, shaped and/or otherwise configured to be passed intraluminally (e.g., intravascularly) through a subject being treated. In various embodiments, the medical instrument 20 comprises a catheter, a shaft, a wire, and/or other elongate instrument. In other embodiments, the medical instrument is not positioned intravascularly but is positioned extravascularly via laparoscopic or open surgical procedures. In various embodiments, the medical instrument 20 comprises a catheter, a shaft, a wire, and/or other elongate instrument. In some embodiments, one or more temperature sensing devices or systems 60 (e.g., thermocouples, thermistors, etc.) may be included at the distal end of the medical instrument 20, or along its elongate shaft or in its handle. The term "distal end" does not necessarily mean the distal terminus or distal end. Distal end could mean the distal terminus or a location spaced from the distal terminus but generally at a distal end portion of the medical instrument 20.

In some embodiments, the medical instrument 20 is operatively coupled to one or more devices or components. For example, as depicted in FIG. 1, the medical instrument 20 can be coupled to a delivery module 40 (such as an energy delivery module). According to some arrangements, the energy delivery module 40 includes an energy generation device 42 that is configured to selectively energize and/or otherwise activate the energy delivery member(s) 30 (for example, radiofrequency electrodes) located along the medical instrument 20. In some embodiments, for instance, the energy generation device 42 comprises a radiofrequency generator, an ultrasound energy source, a microwave energy source, a laser/light source, another type of energy source or generator, and the like, and combinations thereof. In other embodiments, energy generation device 42 is substituted with or use in addition to a source of fluid, such a cryogenic fluid or other fluid that modulates temperature. Likewise, the delivery module (e.g., delivery module 40), as used herein, can also be a cryogenic device or other device that is configured for thermal modulation.

With continued reference to the schematic of FIG. 1, the energy delivery module 40 can include one or more input/output devices or components 44, such as, for example, a touchscreen device, a screen or other display, a controller (e.g., button, knob, switch, dial, etc.), keypad, mouse, joystick, trackpad, or other input device and/or the like. Such devices can permit a physician or other user to enter information into and/or receive information from the system 10. In some embodiments, the output device 44 can include a touchscreen or other display that provides tissue temperature information, contact information, other measurement information and/or other data or indicators that can be useful for regulating a particular treatment procedure.

According to some embodiments, the energy delivery module 40 includes a processor 46 (e.g., a processing or control unit) that is configured to regulate one or more aspects of the treatment system 10. The module 40 can also comprise a memory unit or other storage device 48 (e.g., computer readable medium) that can be used to store operational parameters and/or other data related to the operation of the system 10. In some embodiments, the processor 46 is configured to automatically regulate the delivery of energy from the energy generation device 42 to the energy delivery member 30 of the medical instrument 20 based on one or more operational schemes. For example, energy provided to the energy delivery member 30 (and thus, the amount of heat transferred to or from the targeted tissue) can be regulated based on, among other things, the detected temperature of the tissue being treated.

According to some embodiments, the energy delivery system 10 can include one or more temperature detection devices, such as, for example, reference temperature devices (e.g., thermocouples, thermistors, etc.) and/or the like. For example, in some embodiments, the device further comprises a one or more temperature sensors or other temperature-measuring devices to help determine a peak (e.g., high or peak, low or trough, etc.) temperature of tissue being treated. In some embodiments, the temperature sensors (e.g., thermocouples) located at, along and/or near the ablation member (e.g., RF electrode) can help with the determination of whether contact is being made between the ablation member and targeted tissue (and/or to what degree such contact is being made). In some embodiments, such peak temperature is determined without the use of radiometry.

With reference to FIG. 1, the energy delivery system 10 comprises (or is in configured to be placed in fluid communication with) an irrigation fluid system 70. In some embodiments, as schematically illustrated in FIG. 1, such a fluid system 70 is at least partially separate from the energy delivery module 40 and/or other components of the system 10. However, in other embodiments, the irrigation fluid system 70 is incorporated, at least partially, into the energy delivery module 40. The irrigation fluid system 70 can include one or more pumps or other fluid transfer devices that are configured to selectively move fluid through one or more lumens or other passages of the catheter 20. Such fluid can be used to selectively cool (e.g., transfer heat away from) the energy delivery member 30 during use.

Figure 2:
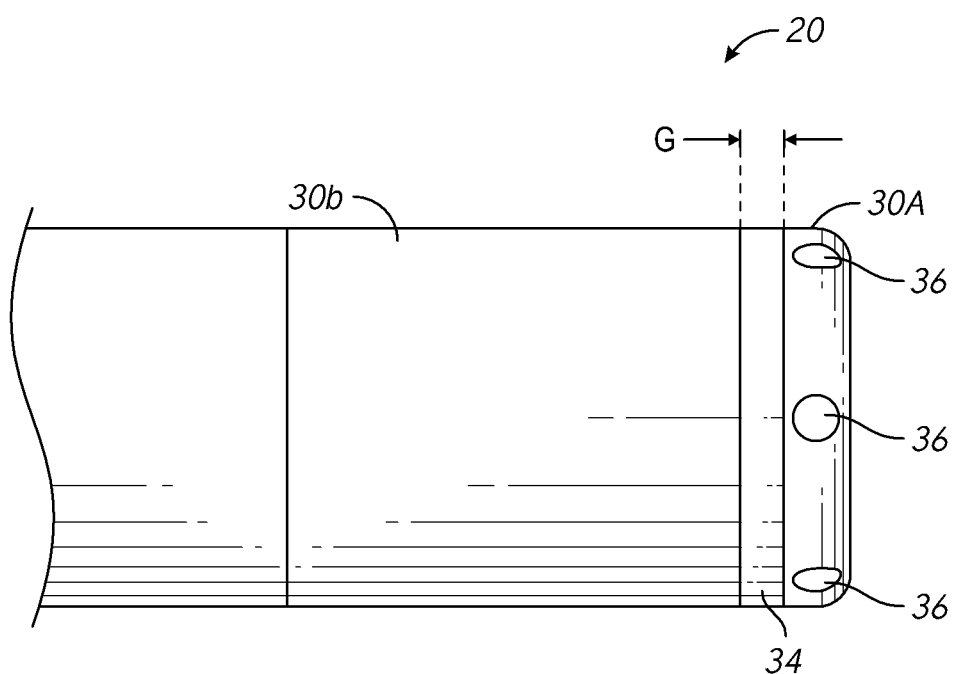
FIG. 2 illustrates a side view of a system's catheter comprises a high-resolution-tip design according to one embodiment.

FIG. 2 illustrates one embodiment of a distal end of a medical instrument (e.g., catheter) 20. As shown, the catheter 20 can include a high-resolution tip design, such that there are two adjacent electrodes or two adjacent electrode portions 30A, 30B separated by a gap G. According to some embodiments, as depicted in the configuration of FIG. 2, the relative length of the different electrodes or electrode portions 30A, 30B can vary. For example, the length of the proximal electrode 30B can be between 1 to 20 times (e.g., 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.) the length of the distal electrode 30A, as desired or required. In other embodiments, the length of the proximal electrode 30B can be greater than 20 times (e.g., 20-25, 25-30, more than 30 times, etc.) the length of the distal electrode 30A. In yet other embodiments, the lengths of the distal and proximal electrodes 30A, 30B are about equal. In some embodiments, the distal electrode 30A is longer than the proximal electrode 30B (e.g., by 1 to 20 times, such as, for example, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.).

In some embodiments, the distal electrode or electrode portion 30A is 0.5 mm long. In other embodiments, the distal electrode or electrode portion 30A is between 0.1 mm and 1 mm long (e.g., 0.1-0.2, 0.2-0.3, 0.3-0.4, 0.4-0.5, 0.5-0.6, 0.6-0.7, 0.-0.8, 0.8-0.9, 0.9-1 mm, values between the foregoing ranges, etc.). In other embodiments, the distal electrode or electrode portion 30A is greater than 1 mm in length, as desired or required. In some embodiments, the proximal electrode or electrode portion 30B is 2 to 4 mm long (e.g., 2-2.5, 2.5-3, 3-3.5, 3.5-4 mm, lengths between the foregoing, etc.). However, in other embodiments, the proximal electrode portion 30B is greater than 4 mm (e.g., 4-5, 5-6, 6-7, 7-8, 8-9, 9-10 mm, greater than 10 mm, etc.) or smaller than 1 mm (e.g., 0.1-0.5 0.5-1, 1-1.5, 1.5-2 mm, lengths between the foregoing ranges, etc.), as desired or required. In embodiments where the high-resolution electrodes are located on catheter shafts, the length of the electrodes can be 1 to 5 mm (e.g., 1-2, 2-3, 3-4, 4-5 mm, lengths between the foregoing, etc.). However, in other embodiments, the electrodes can be longer than 5 mm (e.g., 5-6, 6-7, 7-8, 8-9, 9-10, 10-15, 15-20 mm, lengths between the foregoing, lengths greater than 20 mm, etc.), as desired or required.

As noted above, the use of a high-resolution tip design can permit a user to simultaneously ablate or otherwise thermally treat targeted tissue and map (e.g., using high-resolution mapping) in a single configuration. Thus, such systems can advantageously permit precise high-resolution mapping (e.g., to confirm that a desired level of treatment occurred) during a procedure. In some embodiments, the high-resolution tip design that includes two electrodes or electrode portions 30A, 30B can be used to record a high-resolution bipolar electrogram. For such purposes, the two electrodes or electrode portions can be connected to the inputs of an EP recorder. In some embodiments, a relatively small separation distance (e.g., gap G) between the electrodes or electrode portions 30A, 30B enables high-resolution mapping.

In some embodiments, a medical instrument (e.g., a catheter) 20 can include three or more electrodes or electrode portions (e.g., separated by gaps), as desired or required. Additional details regarding such arrangements are provided below. According to some embodiments, regardless of how many electrodes or electrode portions are positioned along a catheter tip, the electrodes or electrode portions 30A, 30B are radiofrequency electrodes and comprise one or more metals, such as, for example, stainless steel, platinum, platinum-iridium, gold, gold-plated alloys and/or the like.

According to some embodiments, as illustrated in FIG. 2, the electrodes or electrode portions 30A, 30B are spaced apart from each other (e.g., longitudinally or axially) using a gap (e.g., an electrically insulating gap). In some embodiments, the length of the gap G (or the separation distance between adjacent electrodes or electrode portions) is 0.5 mm. In other embodiments, the gap G or separation distance is greater or smaller than 0.5 mm, such as, for example, 0.1-1 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required According to some embodiments, a separator 34 is positioned within the gap G, between the adjacent electrodes or electrode portions 30A, 30B, as depicted in FIG. 2. The separator can comprise one or more electrically insulating materials, such as, for example, Teflon, polyetheretherketone (PEEK), polyetherimide resins (e.g., ULTEM™), ceramic materials, polyimide and the like.

As noted above with respect to the gap G separating the adjacent electrodes or electrode portions, the insulating separator 34 can be 0.5 mm long. In other embodiments, the length of the separator 34 can be greater or smaller than 0.5 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required.

According to some embodiments, as discussed in greater detail herein, to ablate or otherwise heat or treat targeted tissue of a subject successfully with the high-resolution tip electrode design, such as the one depicted in FIG. 2, the two electrodes or electrode portions 30A, 30B are electrically coupled to each other at the RF frequency. Thus, the two electrodes or electrode portions can advantageously function as a single longer electrode at the RF frequency.

Figure 3:
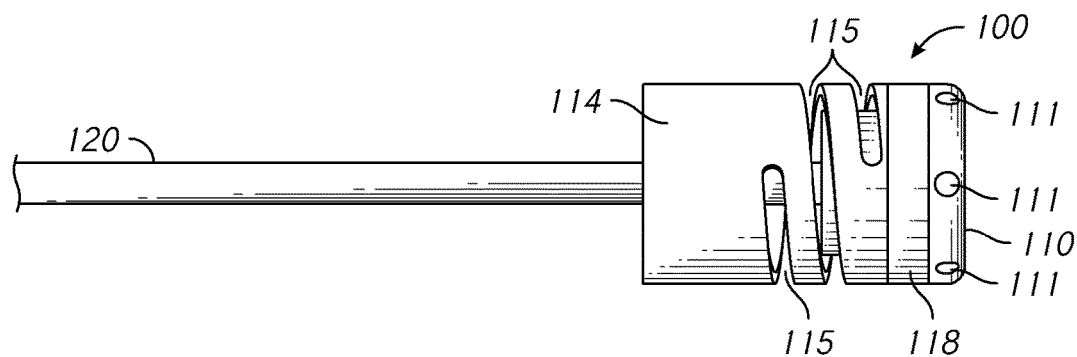
FIG. 3 illustrates a side view of a system's catheter comprises a high-resolution-tip design according to another embodiment.
Figure 4:
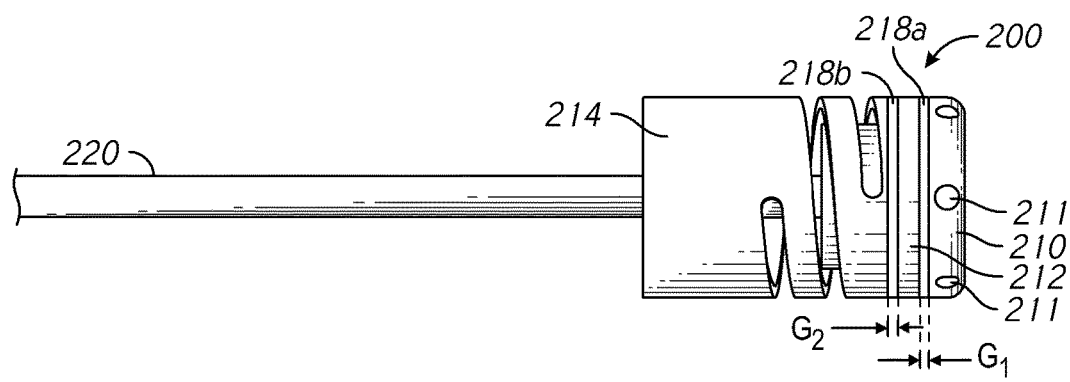
FIG. 4 illustrates a side view of a system's catheter comprises a high-resolution-tip design according to yet another embodiment.

FIGS. 3 and 4 illustrate different embodiments of catheter systems 100, 200 that incorporate a high-resolution tip design. For example, in FIG. 3, the electrode (e.g., radiofrequency electrode) along the distal end of the electrode comprises a first or distal electrode or electrode portion 110 and a second or proximal electrode or electrode portion 114. As shown and discussed in greater detail herein with reference to other configurations, the high-resolution tip design 100 includes a gap G between the first and second electrodes or electrode portions 110, 114. In some configurations, the second or proximal electrode or electrode portion 114 is generally longer than the first or distal electrode or electrode portion 110. For instance, the length of the proximal electrode 114 can be between 1 to 20 times (e.g., 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.) the length of the distal electrode 110, as desired or required. In other embodiments, the length of the proximal electrode can be greater than 20 times (e.g., 20-25, 25-30, more than 30 times, etc.) the length of the distal electrode. In yet other embodiments, the lengths of the distal and proximal electrodes are about the same. However, in some embodiments, the distal electrode 110 is longer than the proximal electrode 114 (e.g., by 1 to 20 times, such as, for example, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.).

As shown in FIG. 3 and noted above, regardless of their exact design, relative length diameter, orientation and/or other characteristics, the electrodes or electrode portions 110, 114 can be separated by a gap G. The gap G can comprise a relatively small electrically insulating gap or space. In some embodiments, an electrically insulating separator 118 can be snugly positioned between the first and second electrodes or electrode portions 110, 114. In certain embodiments, the separator 118 can have a length of about 0.5 mm. In other embodiments, however, the length of the separator 118 can be greater or smaller than 0.5 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required. The separator can include one or more electrically insulating materials (e.g., materials that have an electrical conductivity less than about 1000 or less (e.g., 500-600, 600-700, 700-800, 800-900, 900-1000, 1000-1100, 1100-1200, 1200-1300, 1300-1400, 1400-1500, values between the foregoing, less than 500, greater than 1500, etc.) than the electrical conductivity of metals or alloys). The separator can comprise one or more electrically insulating materials, such as, for example, Teflon, polyetheretherketone (PEEK), polyoxymethylene, acetal resins or polymers and the like.

As shown in FIG. 3, the separator 118 can be cylindrical in shape and can have the identical or similar diameter and configuration as the adjacent electrodes or electrode portions 110, 114. Thus, in some embodiments, the outer surface formed by the electrodes or electrode portions 110, 114 and the separator 118 can be generally uniform or smooth. However, in other embodiments, the shape, size (e.g., diameter) and/or other characteristics of the separator 118 can be different than one or more of the adjacent electrodes or electrode portions 110, 114, as desired or required for a particular application or use.

FIG. 4 illustrates an embodiment of a system 200 having three or more electrodes or electrode portions 210, 212, 214 separated by corresponding gaps G1, G2. The use of such additional gaps, and thus, additional electrodes or electrode portions 210, 212, 214 that are physically separated (e.g., by gaps) yet in close proximity to each other, can provide additional benefits to the high-resolution mapping capabilities of the system. For example, the use of two (or more) gaps can provide more accurate high-resolution mapping data related to the tissue being treated. Such multiple gaps can provide information about the directionality of cardiac signal propagation. In addition, high-resolution mapping with high-resolution electrode portions involving multiple gaps can provide a more extended view of lesion progression during the ablation process and higher confidence that viable tissue strands are not left behind within the targeted therapeutic volume. In some embodiments, high-resolution electrodes with multiple gaps can optimize the ratio of mapped tissue surface to ablated tissue surface. Preferably, such ratio is in the range of 0.2 to 0.8 (e.g., 0.2-0.3, 0.3-0.4, 0.4-0.5, 0.5-0.6, 0.6-0.7, 0.7-0.8, ratios between the foregoing, etc.). Although FIG. 4 illustrates an embodiment having a total of three electrodes or electrode portions 210, 212, 214 (and thus, two gaps G1, G2), a system can be designed or otherwise modified to comprise additional electrodes or electrode portions, and thus, additional gaps. For example, in some embodiments, an ablation or other treatment system can include 4 or more (e.g., 5, 6, 7, 8, more than 8, etc.) electrodes or electrode portions (and thus, 3 or more gaps, e.g., 3, 4, 5, 6, 7 gaps, more than 7 gaps, etc.), as desired or required. In such configurations, a gap (and/or an electrical separator) can be positioned between adjacent electrodes or electrode portions, in accordance with the embodiments illustrated in FIGS. 2 to 4.

As depicted in FIGS. 3 and 4, an irrigation tube 120, 220 can be routed within an interior of the catheter (not shown for clarity). In some embodiments, the irrigation tube 120, 220 can extend from a proximal portion of the catheter (e.g., where it can be placed in fluid communication with a fluid pump) to the distal end of the system. For example, in some arrangements, as illustrated in the side views of FIGS. 3 and 4, the irrigation tube 120, 220 extends and is in fluid communication with one or more fluid ports 211 that extend radially outwardly through the distal electrode 110, 210. Thus, in some embodiments, the treatment system comprises an open irrigation design, wherein saline and/or other fluid is selectively delivered through the catheter (e.g., within the fluid tube 120, 220) and radially outwardly through one or more outlet ports 111, 211 of an electrode 110, 210. The delivery of such saline or other fluid can help remove heat away from the electrodes and/or the tissue being treated. In some embodiments, such an open irrigation system can help prevent or reduce the likelihood of overheating of targeted tissue, especially along the tissue that is contacted by the electrodes. An open irrigation design is also incorporated in the system that is schematically illustrated in FIG. 2. For instance, as depicted in FIG. 2, the distal electrode or electrode portion 34 can include a plurality of outlet ports 36 through which saline or other irrigation fluid can exit.

Figure 5:
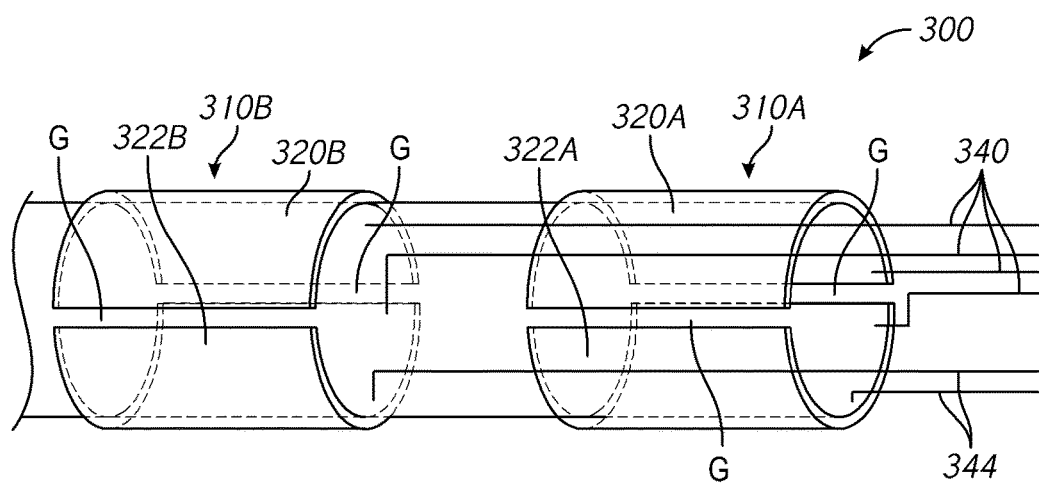
FIG. 5 illustrates an embodiment of a system's catheter comprising two high-resolution-section electrodes each consisting of separate sections circumferentially distributed on the catheter shaft.

According to some embodiments, a catheter can include a high-resolution-tip electrode design that includes one or more gaps in the circumferential direction (e.g., radially), either in addition to or in lieu of gaps in the longitudinal direction. One embodiment of a system 300 comprising one or more electrodes 310A, 310B is illustrated in FIG. 5. As shown, in arrangements where two or more electrodes are included, the electrodes 310A, 310B can be longitudinally or axially offset from each other. For example, in some embodiments, the electrodes 310A, 310B are located along or near the distal end of a catheter. In some embodiments, the electrodes 310A, 310B are located along an exterior portion of a catheter or other medical instrument. However, in other configurations, one or more of the electrodes can be positioned along a different portion of the catheter or other medical instrument (e.g., along at least an interior portion of a catheter), as desired or required.

With continued reference to FIG. 5, each electrode 310A, 310B can comprises two or more sections 320A, 322A and/or 320B, 320B. As shown, in some embodiments, the each section 320A, 322A and/or 320B, 320B can extend half-way around (e.g., 180 degrees) the diameter of the catheter. However, in other embodiments, the circumferential extent of each section can be less than 180 degrees. For example, each section can extend between 0 and 180 degrees (e.g., 15, 30, 45, 60, 75, 90, 105, 120 degrees, degrees between the foregoing, etc.) around the circumference of the catheter along which it is mounted. Thus, in some embodiments, an electrode can include 2, 3, 4, 5, 6 or more circumferential sections, as desired or required.

Regardless of how the circumferential electrode sections are designed and oriented, electrically insulating gaps G can be provided between adjacent sections to facilitate the ability to use the electrode to conduct high-resolution mapping, in accordance with the various embodiments disclosed herein. Further, as illustrated in the embodiment of FIG. 5, two or more (e.g., 3, 4, 5, more than 5, etc.) electrodes 310A, 310B having two or more circumferential or radial sections can be included in a particular system 300, as desired or required.

In alternative embodiments, the various embodiments of a high-resolution tip design disclosed herein, or variations thereof, can be used with a non-irrigated system or a closed-irrigation system (e.g., one in which saline and/or other fluid is circulated through or within one or more electrodes to selectively remove heat therefrom). Thus, in some arrangements, a catheter can include two or more irrigation tubes or conduits. For example, one tube or other conduit can be used to deliver fluid toward or near the electrodes, while a second tube or other conduit can be used to return the fluid in the reverse direction through the catheter.

According to some embodiments, a high-resolution tip electrode is designed to balance the current load between the various electrodes or electrode portions. For example, if a treatment system is not carefully configured, the electrical load may be delivered predominantly to one or more of the electrodes or electrode portions of the high-resolution tip system (e.g., the shorter or smaller distal electrode or electrode portion). This can lead to undesirable uneven heating of the electrode, and thus, uneven heating (e.g., ablation) of the adjacent tissue of the subject. Thus, in some embodiments, one or more load balancing configurations can be used to help ensure that the heating along the various electrodes or electrode portions of the system will be generally balanced. As a result, the high-resolution tip design can advantageously function more like a longer, single electrode, as opposed to two or more electrodes that receive an unequal electrical load (and thus, deliver an unequal amount of heat or level of treatment to the subject's targeted tissue).

Figure 6:
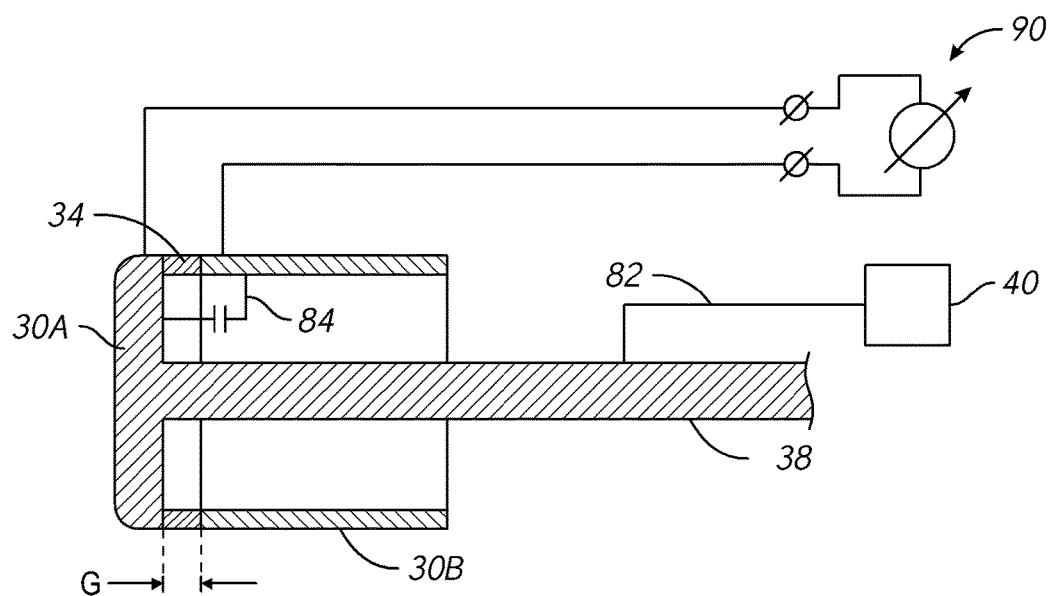
FIG. 6 schematically illustrates one embodiment of a high-pass filtering element consisting of a coupling capacitor. The filtering element can be incorporated into a system's catheter that comprises a high-resolution-tip design.

One embodiment of a configuration that can be used to balance the electrical current load delivered to each of the electrodes or electrode portions in a high-resolution tip design is schematically illustrated in FIG. 6. As shown, one of the electrodes (e.g., the distal electrode) 30A can be electrically coupled to an energy delivery module 40 (e.g., a RF generator). As discussed herein, the module 40 can comprise one or more components or features, such as, for example, an energy generation device that is configured to selectively energize and/or otherwise activate the energy members (e.g., RF electrodes), one or more input/output devices or components, a processor (e.g., a processing or control unit) that is configured to regulate one or more aspects of the treatment system, a memory and/or the like. Further, such a module can be configured to be operated manually or automatically, as desired or required.

In the embodiment that is schematically depicted in FIG. 6, the distal electrode 30A is energized using one or more conductors 82 (e.g., wires, cables, etc.). For example, in some arrangements, the exterior of the irrigation tube 38 comprises and/or is otherwise coated with one or more electrically conductive materials (e.g., copper, other metal, etc.). Thus, as shown in FIG. 6, the conductor 82 can be placed in contact with such a conductive surface or portion of the tube 38 to electrically couple the electrode or electrode portion 30A to an energy delivery module. However, one or more other devices and/or methods of placing the electrode or electrode portion 30A in electrical communication with an energy delivery module can be used. For example, one or more wires, cables and/or other conductors can directly or indirectly couple to the electrodes, without the use of the irrigation tube.

With continued reference to FIG. 6, the first or distal electrode or electrode portion 30A can be electrically coupled to the second or proximal electrode or electrode portion 30B using one more band-pass filtering elements 84, such as a capacitor, a filter circuit (see, e.g., FIG. 16), etc. For instance, in some embodiments, the band-pass filtering element 84 comprises a capacitor that electrically couples the two electrodes or electrode portions 30A, 30B when radiofrequency current is applied to the system. In one embodiment, the capacitor 84 comprises a 100 nF capacitor that introduces a series impedance lower than about 3Ω at 500 kHz, which, according to some arrangements, is a target frequency for RF ablation. However, in other embodiments, the capacitance of the capacitor(s) or other band-pass filtering elements 84 that are incorporated into the system can be greater or less than 100 nF, for example, 5 nF to 300 nF, according to the operating RF frequency, as desired or required. In some embodiments, the capacitance of the filtering element 84 is selected based on a target impedance at a particular frequency or frequency range. For example, in some embodiments, the system can be operated at a frequency of 200 kHz to 10 MHz (e.g., 200-300, 300-400, 400-500, 500-600, 600-700, 700-800, 800-900, 900-1000 kHz, up to 10 MHz or higher frequencies between the foregoing ranges, etc.). Thus, the capacitor that couples adjacent electrodes or electrode portions to each other can be selected based on the target impedance for a particular frequency. For example, a 100 nF capacitor provides about 3Ω of coupling impedance at an operating ablation frequency of 500 kHz.

In some embodiments, a series impedance of 3Ω across the electrodes or electrode portions 30A, 30B is sufficiently low when compared to the impedance of the conductor 82 (e.g., wire, cable, etc.), which can be about 5-10Ω, and the impedance of tissue, which can be about 100Ω, such that the resulting tissue heating profile is not negatively impacted when the system is in use. Thus, in some embodiments, a filtering element is selected so that the series impedance across the electrodes or electrode portions is lower than the impedance of the conductor that supplies RF energy to the electrodes. For example, in some embodiments, the insertion impedance of the filtering element is 50% of the conductor 82 impedance, or lower, or 10% of the equivalent tissue impedance, or lower.

Figure 16:
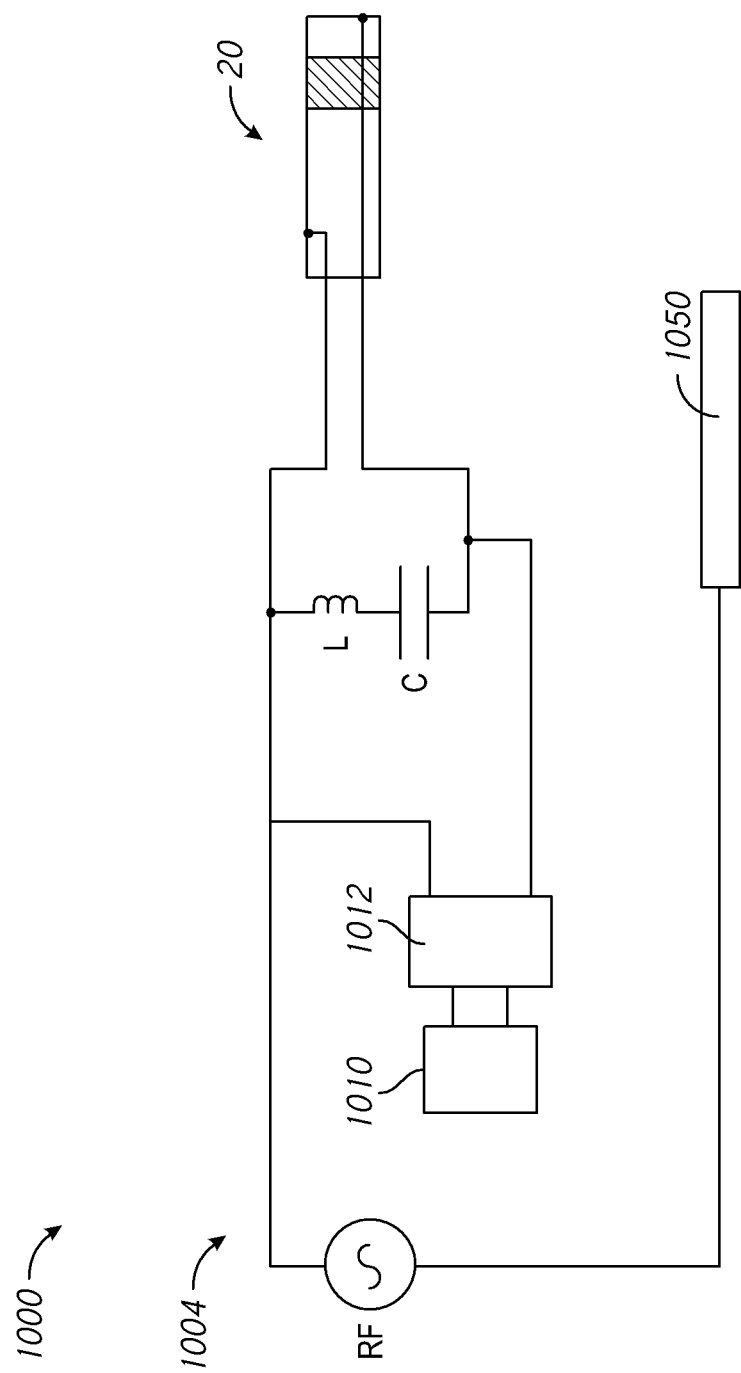
FIG. 16 schematically illustrates an alternate embodiment of a filtering element comprising a circuit configured to be used with any of the devices and systems disclosed herein to facilitate high resolution mapping.

In some embodiments, a filtering element (e.g., capacitor a filter circuit such as the one described herein with reference to FIG. 16, etc.) can be located at a variety of locations of the device or accompanying system. For example, in some embodiments, the filtering element is located on or within a catheter (e.g., near the distal end of the catheter, adjacent the electrode, etc.). In other embodiments, however, the filtering element is separate of the catheter. For instance, the filtering element can be positioned within or along a handle to which the catheter is secured, within the generator or other energy delivery module, within a separate processor or other computing device or component and/or the like).

Figure 7:
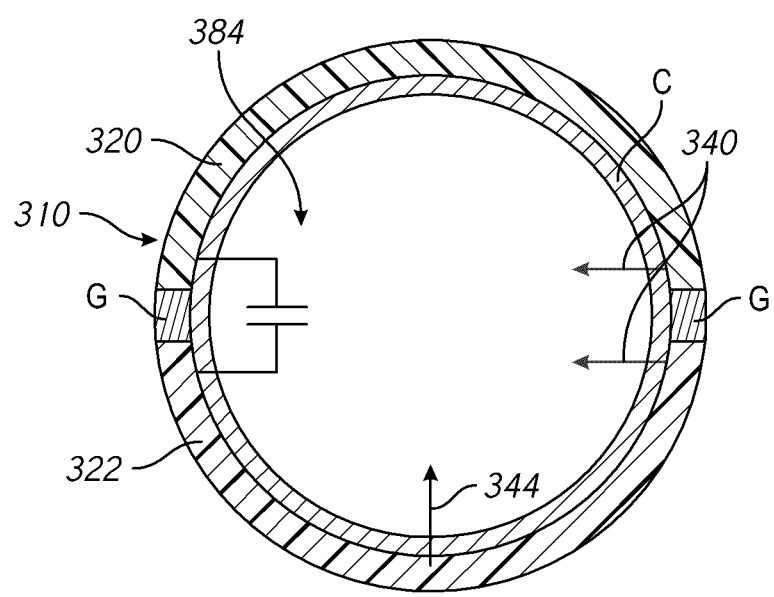
FIG. 7 schematically illustrates one embodiment of four high-pass filtering elements comprising coupling capacitors. The filtering elements can operatively couple, in the operating RF frequency range, the separate electrode sections of a system's catheter electrodes, e.g., those illustrated in FIG. 5.

Similarly, with reference to the schematic of FIG. 7, a filtering element 384 can be included in an electrode 310 comprising circumferentially-arranged portions 320, 322. In FIG. 7, the filtering element 384 permits the entire electrode 310 to be energized within RF frequency range (e.g., when the electrode is activated to ablate). One or more RF wires or other conductors 344 can be used to deliver power to the electrode from a generator or source. In addition, separate conductors 340 can be used to electrically couple the electrode 310 for mapping purposes.

In embodiments where the high-resolution-tip design (e.g., FIG. 4) comprises three or more electrodes or electrode portions, additional filtering elements (e.g., capacitors) can be used to electrically couple the electrodes or electrode portions to each other. Such capacitors or other filtering elements can be selected to create a generally uniform heating profile along the entire length of the high-resolution tip electrode. As noted in greater detail herein, for any of the embodiments disclosed herein or variations thereof, the filtering element can include something other than a capacitor. For example, in some arrangements, the filtering element comprises a LC circuit (e.g., a resonant circuit, a tank circuit, a tuned circuit, etc.). Such embodiments can be configured to permit simultaneous application of RF energy and measurement of EGM recordings.

As discussed above, the relatively small gap G between the adjacent electrodes or electrode portions 30A, 30B can be used to facilitate high-resolution mapping of the targeted tissue. For example, with continued reference to the schematic of FIG. 6, the separate electrodes or electrode portions 30A, 30B can be used to generate an electrogram that accurately reflects the localized electrical potential of the tissue being treated. Thus, a physician or other practitioner using the treatment system can more accurately detect the impact of the energy delivery to the targeted tissue before, during and/or after a procedure. For example, the more accurate electrogram data that result from such configurations can enable the physician to detect any gaps or portions of the targeted anatomical region that was not properly ablated or otherwise treated. Specifically, the use of a high-resolution tip design can enable a cardiac electrophysiologist to more accurately evaluate the morphology of a resulting electrograms, their amplitude and width and/or to determine pacing thresholds. In some embodiments, morphology, amplitude and pacing threshold are accepted and reliable EP markers that provide useful information about the outcome of an ablation or other heat treatment procedure.

Figure 8:
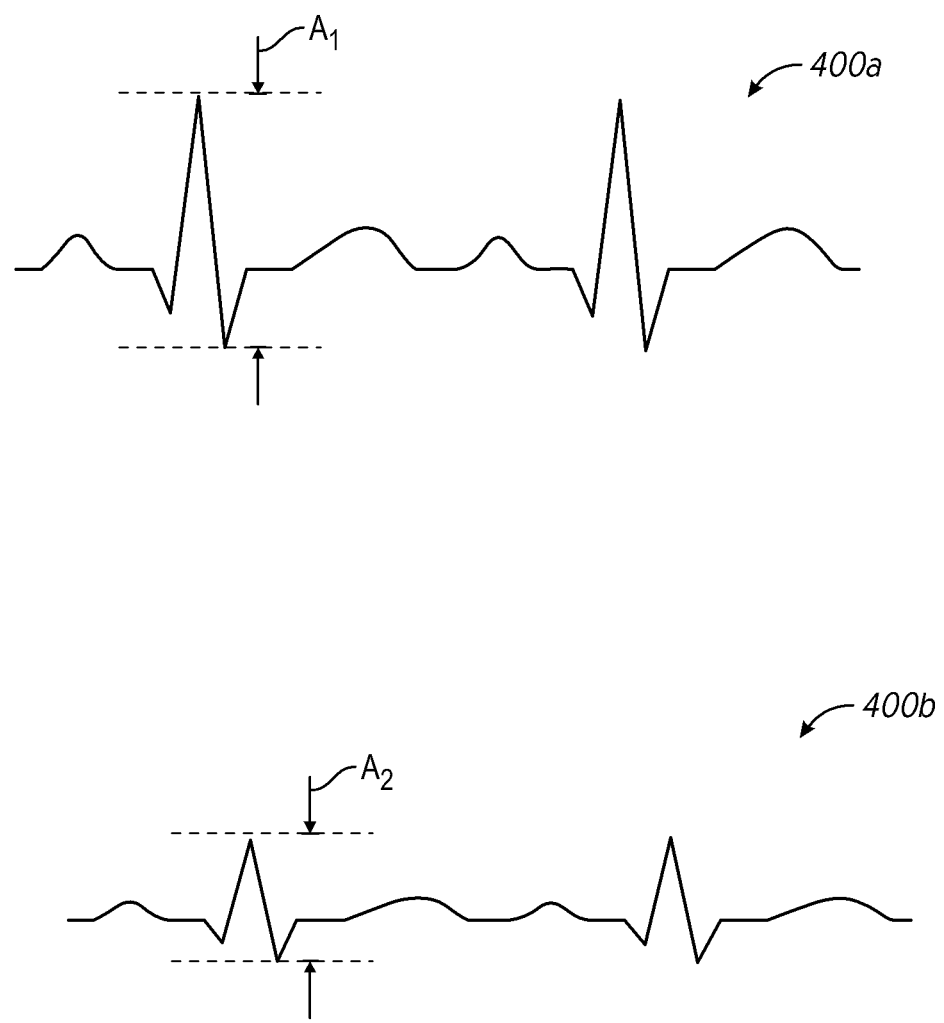
FIG. 8 illustrates embodiments of EKGs obtained from a high-resolution-tip electrode systems disclosed herein configured to detect whether an ablation procedure has been adequately performed.

According to some arrangements, the high-resolution-tip electrode embodiments disclosed herein are configured to provide localized high-resolution electrogram. For example, the electrogram that is obtained using a high-resolution-tip electrode, in accordance with embodiments disclosed herein, can provide electrogram data (e.g., graphical output) 400a, 400b as illustrated in FIG. 8. As depicted in FIG. 8, the localized electrograms 400a, 400b generated using the high-resolution-tip electrode embodiments disclosed herein include an amplitude A1, A2.

With continued reference to FIG. 8, the amplitude of the electrograms 400a, 400b obtained using high-resolution-tip electrode systems can be used to determine whether targeted tissue adjacent the high-resolution-tip electrode has been adequately ablated or otherwise treated. For example, according to some embodiments, the amplitude A1 of an electrogram 400a in untreated tissue (e.g., tissue that has not been ablated or otherwise heated) is greater that the amplitude A2 of an electrogram 400b that has already been ablated or otherwise treated. In some embodiments, therefore, the amplitude of the electrogram can be measured to determine whether tissue has been treated. For example, the electrogram amplitude A1 of untreated tissue in a subject can be recorded and used as a baseline. Future electrogram amplitude measurements can be obtained and compared against such a baseline amplitude in an effort to determine whether tissue has been ablated or otherwise treated to an adequate or desired degree.

In some embodiments, a comparison is made between such a baseline amplitude (A1) relative to an electrogram amplitude (A2) at a tissue location being tested or evaluated. A ratio of A1 to A2 can be used to provide a quantitative measure for assessing the likelihood that ablation has been completed. In some arrangements, if the ratio (i.e., A1/A2) is above a certain minimum threshold, then the user can be informed that the tissue where the A2 amplitude was obtained has been properly ablated. For example, in some embodiments, adequate ablation or treatment can be confirmed when the A1/A2 ratio is greater than 1.5 (e.g., 1.5-1.6, 1.6-1.7, 1.7-1.8, 1.8-1.9, 1.9-2.0, 2.0-2.5, 2.5-3.0, values between the foregoing, greater than 3, etc.). However, in other embodiments, confirmation of ablation can be obtained when the ratio of A1/A2 is less than 1.5 (e.g., 1-1.1, 1.1-1.2, 1.2-1.3, 1.3-1.4, 1.4-1.5, values between the foregoing, etc.).

Figure 9:
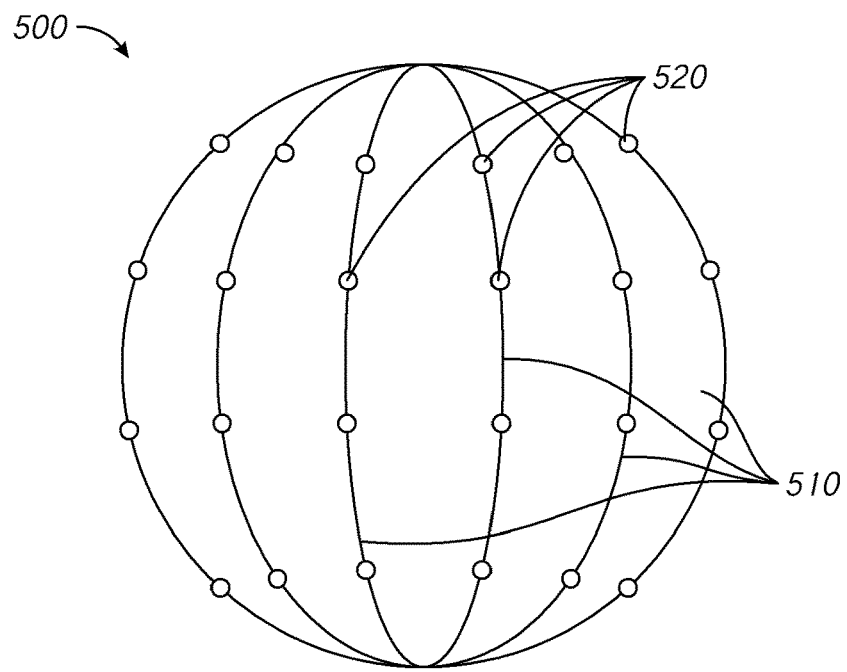
FIG. 9 illustrates one embodiment of a commercially-available mapping system comprising a plurality of mapping electrodes.

FIG. 9 illustrates one embodiment of an expandable system 500 comprising a plurality of mapping electrodes 520. Such systems 500 can include one or more expandable members (e.g., struts, balloons, etc.) 510 that support the electrodes 520 and help place such electrodes in contact or otherwise in close proximity to a subject tissue. For example, the depicted embodiment of a mapping system 500 comprises a generally spherical configuration when expanded. In some embodiments, such a system 500 is sized, shaped and/or otherwise configured to be positioned and expanded within a heart chamber (e.g., atrium, ventricle) of a subject. In some arrangements, the struts comprise sufficient resiliency, stability, flexibility and/or other properties to enable the expanded system 500 to conform or generally conform to the bodily cavity or other space (e.g., atrium) in which it is positioned. Although one representation of a commercially-available system is depicted in FIG. 9, such systems with mapping electrodes can include any other shape, size and/or configuration, depending on one or more factors and/or other considerations, such as, for example, the targeted tissue of the subject, the number of electrodes that are desired or necessary and/or the like. For example, in other embodiments, such systems can include more or fewer electrodes, a non-spherical shape (e.g., conical, cylindrical, irregular, etc.) and/or the like, as desired or required for a particular application or use.

Regardless of the exact design, configuration and/or other properties of a commercially-available mapping system that may be utilized, the electrodes included within the mapping system can vary, as desired or required. For example, in some embodiments, the electrodes 520 comprise unipolar or bipolar electrodes. In addition, the shape, size, configuration and/or other details of the electrodes 520 used in such systems 500 may vary, based on the specific system design.

According to some embodiments, such mapping systems 500 are utilized to help map a subject's cardiac chamber (e.g., atrium) during a cardiac fibrillation (e.g., atrial fibrillation) treatment. For example, in some instances, subjects that indicate for atrial fibrillation exhibit an atrial fibrillation rotor pattern in their atrium that is characteristic of the disease. In some arrangements, electrically mapping the signals being transmitted through a subject's atrium, and thus, more accurately determining a map of the corresponding atrial fibrillation rotor that is cause of the disease, can assist with the subject treatment of the subject. For example, in some embodiments, once the atrial fibrillation rotor is accurately mapped, a practitioner can more precisely treat the portions of the atrium that help treat the disease. This can provide several benefits to a subject, including more precise and accurate ablation that increases the likelihood of effective treatment, less trauma to the subject as area or volume of tissue that is ablated can be reduced and/or the like.

In some embodiments, however, commercially-available mapping systems 500, such as the one schematically illustrated in FIG. 9, have certain shortcomings. For example, depending on how the system is positioned within the targeted anatomical area and/or how the system is deployed, one or more regions of the targeted anatomical volume, space or other region may not be close to a mapping electrode 520. For example, in some embodiments, the splines or other expandable members 510 of a system are not evenly deployed. In other instances, such expandable members 510, for one or more reasons, may not even expand properly or may not expand as intended or expected. As a result, in some cases, mapping electrodes 520 do not properly contact the targeted tissue and/or may leave relatively large areas of tissue between them. Accordingly, under such circumstances, the ability of such systems 500 to accurately map a targeted region of the subject's anatomy may be negatively impacted.

Figure 10:
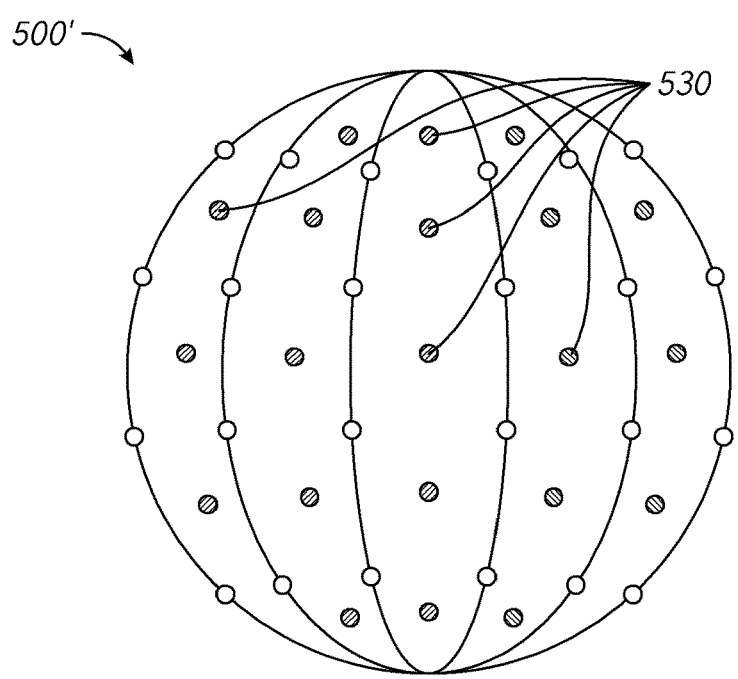
FIG. 10 illustrates one embodiment of intermediate locations that can be mapped by an embodiment of a high-resolution-tip system disclosed herein to obtain a more accurate and comprehensive map of treated tissue.

Therefore, according to some embodiments, a high-resolution-tip electrode catheter system, identical or similar to the systems and devices disclosed herein, can be used as a roving or gap-filling system to create a more accurate and complete electrical map of the targeted anatomical area. Thus, in some embodiments, the system and related methods disclosed herein do not rely solely on the various electrodes of a multi-electrode system or device in order to obtain a map (e.g., three-dimensional map) of tissue being mapped (e.g., cardiac tissue). By way of example, as illustrated schematically in FIG. 10, one or more gaps between the mapping electrodes 520 of a separate mapping system 500 can be "filled" or otherwise addressed from a mapping perspective using the high-resolution capabilities of the high-resolution-tip design. Accordingly, as schematically illustrated in FIG. 10, a high-resolution-tip electrode system can be directed to locations 530 where additional mapping data are required or desired.

In some arrangements, a catheter in accordance with any of the high-resolution-tip embodiments disclosed herein (e.g., those illustrated and discussed herein with reference to FIGS. 1 to 7) can be manually or positioned in some intermediate regions (e.g., regions where a mapping system's electrodes were unable to reach or cover). Thus, by using the high-resolution-tip electrode system as a roving mapping system, more accurate and comprehensive electrical mapping can be accomplished. As a result, in some embodiments, such a roving system (e.g., a catheter comprising a high-resolution electrode) is adapted to obtain mapping data for intermediate tissue locations (e.g., tissue locations located between electrodes of an expandable mapping system or other multi-electrode system or device). As noted above, this can result in a more complete and accurate understanding of the subject's disease and how to more efficiently, safely and effectively treat it. Relatedly, the number of individual ablations (and thus, the total area or volume of tissue that will be ablated) can be advantageously reduced, thereby reducing the overall trauma to the subject, reducing and otherwise mitigating the likelihood of any negative side effects from a treatment procedure, reducing recovery time and/or providing one or more additional advantages or benefits.

Figure 11:
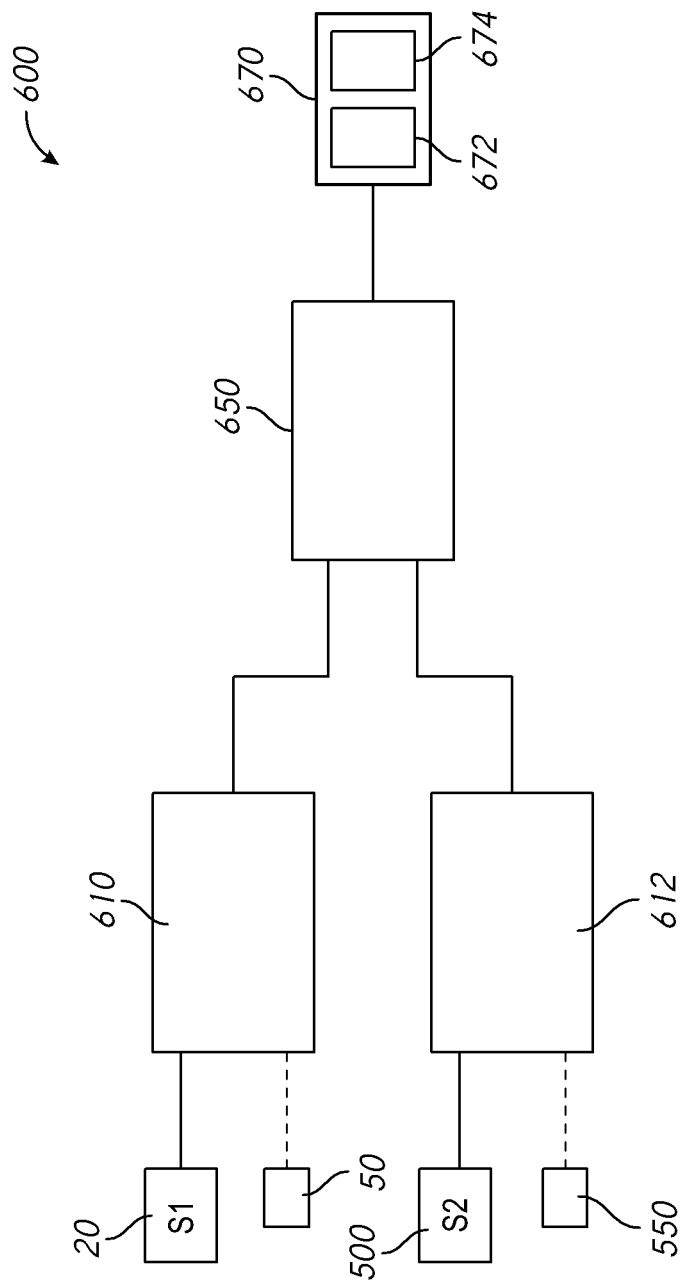
FIG. 11 illustrates a schematic of a mapping system configured to obtain tissue mapping data using at least two different devices according to one embodiment.

FIG. 11 illustrates a schematic of a mapping system 600 configured to obtain tissue mapping data using at least two different devices. For example, in the illustrated embodiment, the system 600 comprises a first device or system (S1) 20 and a second system (S2) 500. According to some embodiments, the first system 20 includes a roving catheter (e.g., comprising a high-resolution-tip design) in accordance with the various configurations disclosed herein or variations thereof. Further, in some embodiments, the second device or system (S2) 500 comprises a plurality of mapping electrodes (e.g., an expandable, catheter-based mapping system that includes electrodes along different splines and/or other expandable members).

With continued reference to the schematic of FIG. 11, depending on the type of electrode(s) that are included in each of the first and second devices or systems 20, 500, the mapping system 600 can include one or more reference electrodes 50, 550. For example, such reference electrodes may be necessary to obtain the necessary mapping data if the electrodes are unipolar. Therefore, in some embodiments, reference electrodes are unnecessary and thus optional and/or not included. By way of example, reference electrodes 50, 550 may be unnecessary if the first and/or the second devices or systems 20, 500 comprise bipolar electrodes (e.g., having a high-resolution-tip design). As discussed herein, in some embodiments, second device or system 500 can include a multi-electrode design that is configured to obtain a plurality of mapping data points at once. For example, second system 500 can include one or more expandable members (e.g., splines, struts, balloons, other inflatable members, other mechanically expandable members or features, etc.). In some embodiments, each such expandable member can include one or more electrodes (e.g., unipolar, bipolar, etc.) that are configured to contact a certain region of the targeted anatomical region (e.g., atrium, ventricle, etc.) upon expansion of the second system 500. Thus, the various electrodes included in the second system 500 can be used to simultaneously obtain several different mapping data points within the targeted anatomical structure of a subject.

However, as noted herein, it may be desirable and beneficial to obtain additional mapping data at locations of the targeted anatomical structure that are between the specially-preset or predetermined locations associated with each of the electrodes of the second device or system 500. In some instances, the second device or system 500 may not be able to cover the entire desired extent or surface coverage or border of the targeted anatomical structure due to anatomical constraints or size or other physical, structural or operational constraints of the second system 500, thereby preventing a complete mapping of the targeted anatomical structure using the second system 500 alone. Accordingly, in some embodiments, a roving system, such as, for example, a catheter comprising a high-resolution-tip design (e.g., such as the various catheter systems disclosed herein) can be used to obtain such intermediate or additional mapping data. The roving system may also be used to determine anatomic region or tissue borders (e.g., superior vena cava border and pulmonary vein tissue borders).

With continued reference to the schematic of FIG. 11, the first device or system 20 (e.g., a catheter-based high-resolution-tip system, another type of roving mapping system, etc.) can be operatively coupled to a first data acquisition device or subsystem 610. Likewise, the second device or system 500 (e.g., multi-electrode mapping system) can be operatively coupled to another data acquisition device or subsystem 612. As illustrated schematically in FIG. 11, each of the data acquisition devices or subsystems 610, 612 can be placed in data communication and/or otherwise operatively coupled to a processor or other control module 650. In some embodiments, the mapping system 600 further comprises an output device 670 (e.g., monitor, other display, a computing device, etc.) that is operatively coupled to the processor 650 and is configured to provide mapping data and/or other information to the user. For example, such an output device 670 can include a graphical and/or numerical representation of the mapping data 672 obtained by the first and second devices or systems 20, 500. The output device 670 can additionally provide cardiac signal data (e.g., ECG) and/or the like, as desired or required. In some embodiments, the output device 670 can further include a user input component (e.g., a keypad, keyboard, touchscreen, etc.) to permit the user to enter instructions, information, data and/or the like. Such a user input component 674 can be integrated into the output device 670, as would be the case if the output device 670 included a touchscreen. However, in other embodiments, the system 600 comprises a separate user input device that is operatively coupled to the processor 650, the output device 670 and/or any other component of the system 600, as desired or required.

In some embodiments, regardless of the exact configuration of an enhanced mapping system, such as the one illustrated in FIG. 11 and described herein, the processor 650 of such a system 600 is adapted to combine mapping data from a multi-electrode mapping system with data from a roving system (e.g., a catheter having a high-resolution-tip electrode and/or another electrode design capable of mapping). The combined mapping data obtained by the two mapping devices or systems 20, 500 can be advantageously combined within the processor 650 to provide an enhanced (e.g., more accurate, more complete) 3D map. As discussed in greater detail herein (e.g., with reference to FIG. 14), the processor 650 of the system 600 can be adapted to "align" the data from the two different mapping devices or systems 20, 500 as part of creating the enhanced three-dimensional (3D) map.

As discussed above, the multi-electrode mapping device or system 500 and/or the roving device or system 20 can include one or more bipolar mapping electrodes (e.g., high-resolution-tip electrodes). Thus, in such configurations, the electrodes can be used to obtain mapping data without the use of a reference electrode. However, in some embodiments, the multi-electrode mapping device or system 500 and/or the roving device or system 20 can include one or more unipolar mapping electrodes. In such arrangements, the need exists for one or more reference electrodes in order to obtain the desired mapping data for those unipolar electrodes. Thus, in some embodiments, the mapping system 600 can include one or more reference electrodes. Such reference electrodes can be located external to the subject (e.g., an electrode secured to the subject's skin, such as, for example, a right leg electrode) and/or internal to the subject (e.g., within the subject's superior or inferior vena cava or other vessel), as desired or required.

Figure 12:
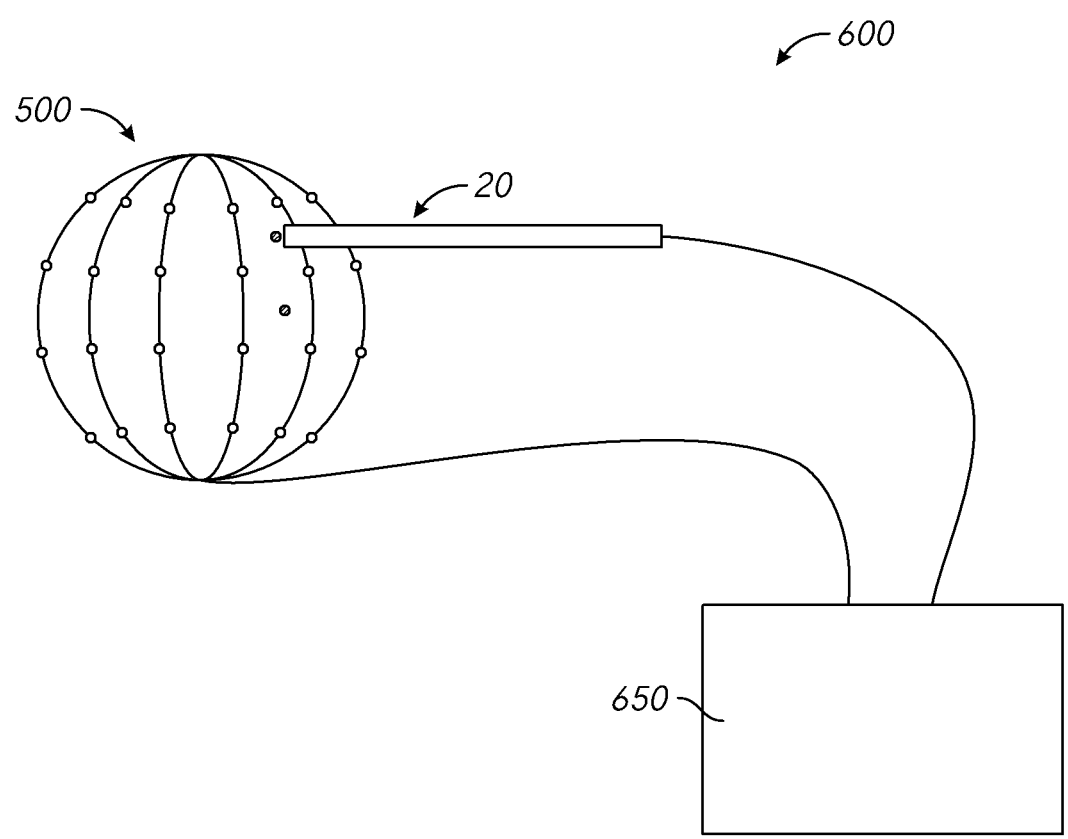
FIG. 12 schematically illustrates one embodiment of an enhanced mapping system that includes a mapping system having a plurality of mapping electrodes and a roving system.

FIG. 12 schematically illustrates one embodiment of an enhanced mapping system 600 that includes a mapping device or system 500 having a plurality of mapping electrodes and a roving device or system 20 (e.g., a catheter with a high-resolution-tip electrode configuration, a catheter with another type of unipolar or bipolar electrode for mapping, etc.). As schematically depicted in FIG. 11, each of the mapping devices or systems 20, 500 can be operatively coupled to a processor or control unit 650 that is configured to retrieve the mapping data obtained by each of the systems or devices 20, 500 and generate an enhanced 3D map or other output of the targeted anatomical region being mapped. In FIG. 12, the additional data points obtained by the roving mapping device or system (e.g., the catheter with a high-resolution-tip design) are illustrated as dots or points between the set electrode locations of the multi-electrode system or device 500. Thus, as noted in greater detail herein, a user can obtain additional mapping data points to create a more accurate and complete 3D map of the targeted anatomical region being mapped (e.g., the atrium, the ventricle, another region within or near the heart, another anatomical region altogether, etc.).

Figure 13:
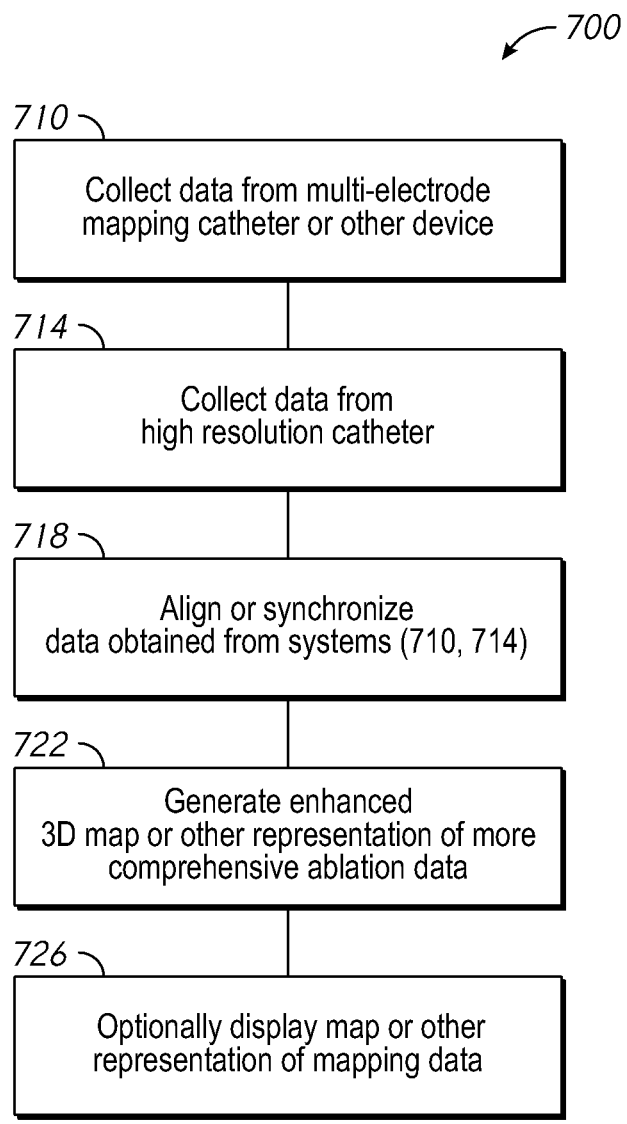
FIG. 13 illustrates one embodiment of an algorithm used by an enhanced mapping system to create an enhanced 3D map of a targeted anatomical region being mapped.

FIG. 13 illustrates one embodiment of an algorithm used by an enhanced mapping system (e.g., such as the configurations disclosed herein, including, without limitation, the system 600 of FIGS. 11 and 12) to create an enhanced 3D map of a targeted anatomical region being mapped. As depicted in FIG. 13, in some embodiments, data is collected (block 710) from a multi-electrode device or system (e.g., the multi-electrode mapping device or system 500 of FIGS. 11 and 12). Further, the mapping system can collect data (block 714) from a high resolution catheter or other device or system (e.g., such as a catheter having a high-resolution-tip electrode or other high-resolution electrode design). In some embodiments, the data obtained from each of the mapping systems or devices 20, 500 is aligned or synchronized (block 718) by the system. Such a step can help normalize the mapping data so that the mapping data accurately reflect the state of the various tissue locations being mapped.

With continued reference to FIG. 13, the system can generate (block 722) an enhanced 3D map of the anatomical region being mapped. At block 726, such mapping data can optionally be provided to a display in order to visually or graphically provide information to the user regarding the tissue being mapped. Alternatively, the mapping data can be saved on a storage device for future processing and review. In some embodiments, the display is integrated with the system. Alternatively, however, the system can be configured to operatively couple to a separate display that is not provided or included with the system.

According to some embodiments, a mapping system can include one or more of the following components: a high-resolution mapping catheter (e.g., a roving catheter), a device having a plurality of mapping electrodes (e.g., configured to produce unipolar and/or bipolar signals), a generator or other energy delivery module, a processor (e.g., which can be included within a generator or other energy delivery module, another component of the system, etc.), a display for displaying mapping data (e.g., in the form of an enhanced three-dimensional map), a user input device and/or any other component. For example, in some embodiments, the system comprises only a generator, other energy delivery module and/or other component comprising a processor that is configured to receive data from two or more mapping devices (e.g., a multi-electrode device, a roving catheter device, etc.). In such embodiments, the processor can receive mapping data from each device and create an enhanced three-dimensional map of the targeted tissue.

In other embodiments, the mapping system comprises only high resolution mapping catheter that is configured to be used with a separate multi-electrode device. As discussed in greater detail herein, mapping data obtained using such a high resolution catheter can be provided to a processor. Such a processor can also be configured to receiving mapping data from a separate mapping system (e.g., a multi-electrode mapping system), and combine the mapping data from the two systems to create an enhanced three-dimensional map of the targeted area. In some embodiments, although it may not be provided with the system, the processor can be included as part of the high-resolution catheter or the multi-electrode mapping device or other separate mapping device. In yet other embodiments, the processor can be included as a stand-alone device or component that is not provided with either the mapping catheter or the multi-electrode (or other) mapping device. Thus, in such arrangements, a separate processor (e.g., positioned within a device) can be used to connect two different mapping systems. Such a processor can be configured to operatively couple to two or more different mapping devices and/or systems (e.g., via wired, wireless and/or other connections). The processor can receive mapping data from each of the mapping devices and/or systems and to generate an enhanced three dimensional map.

According to some embodiments, a mapping system comprises one or more of the following devices and/or components: a high resolution catheter, an expandable device including a plurality of mapping electrodes, separate data acquisition devices configured to receive data from the high-resolution catheter and a multi-electrode mapping device (e.g., expandable device with mapping electrodes), a data acquisition device configured to receive data from both the multi-electrode mapping device and a multi-electrode mapping device, a processor configured to receive the mapping data from one or more data acquisition devices and to process said data to create an enhanced map (e.g., a three-dimensional map of the targeted tissue), an integrated data acquisition device and processor configured to receive mapping data from both the high-resolution catheter and mapping electrodes from a separate expandable device and to process said data to create an enhanced map (e.g., a three-dimensional map of the targeted tissue), a display or other output configured to visually display data and/or graphics related to a map (e.g., a three-dimensional map) of the mapping data obtained and processed by the mapping system and/or one or more other components, devices and/or systems, as desired or required.

By way of example, in one embodiment, the mapping system comprises a high resolution catheter, an expandable device comprising a plurality of mapping electrodes, a data acquisition device configured to receive mapping data from both the high-resolution catheter and the mapping electrodes of expandable mapping device. In such configurations, the system can further include a processor configured to receive the mapping data from the data acquisition device and to process such (e.g., align the data) to generate an enhanced map (e.g., a three-dimensional map) of the tissue. In some embodiments, the system comprises (or is otherwise configured to operatively couple, e.g., via a wired or wireless connection) to a display or other output device.

In accordance with the specific embodiment described above, mapping data are acquired from various mapping electrodes of an expandable system (e.g., a basket) and from a roving catheter having a high-resolution electrode. The catheter can be selectively moved within one or more gaps located between the electrodes of the expandable system to create a more complete and comprehensive map. The mapping data from the two different devices can be acquired by a single device, component and/or system (e.g., a device or component associated with or part of the high-resolution electrode catheter, a device or component associated with or part of the multi-electrode device, etc.). Further, as described in at least some of embodiments disclosed herein, a separate processor (e.g., processor 650) can be used to obtain the mapping data of the high-resolution catheter and the mapping electrodes of an expandable system. Such a processor can receive the mapping data and integrate them (e.g., align them) in order to be able to produce an enhanced three-dimensional map of the targeted tissue.

In other embodiments, the same device, component and/or system that acquires the mapping data from the two different devices is also configured to process such data and create an enhanced map (e.g., a three-dimensional map) of the targeted tissue. Such a single data acquisition device and processor can be part of the expandable system, the system that comprises the high-resolution catheter or a separate device, component and/or a separate system altogether, as desired or required.

In yet other embodiments, each of the high-resolution catheter device and a multi-electrode mapping device comprises a separate data acquisition device (e.g., the system does not include a single data acquisition device that is configured to receive mapping data from two separate devices). In such embodiments, the data acquired from each of the data acquisition devices can be provided to a separate processor to process the data (e.g. integrate the data) and to produce an enhanced map (e.g., a three-dimensional map) of the tissue being mapped.

Figure 14:
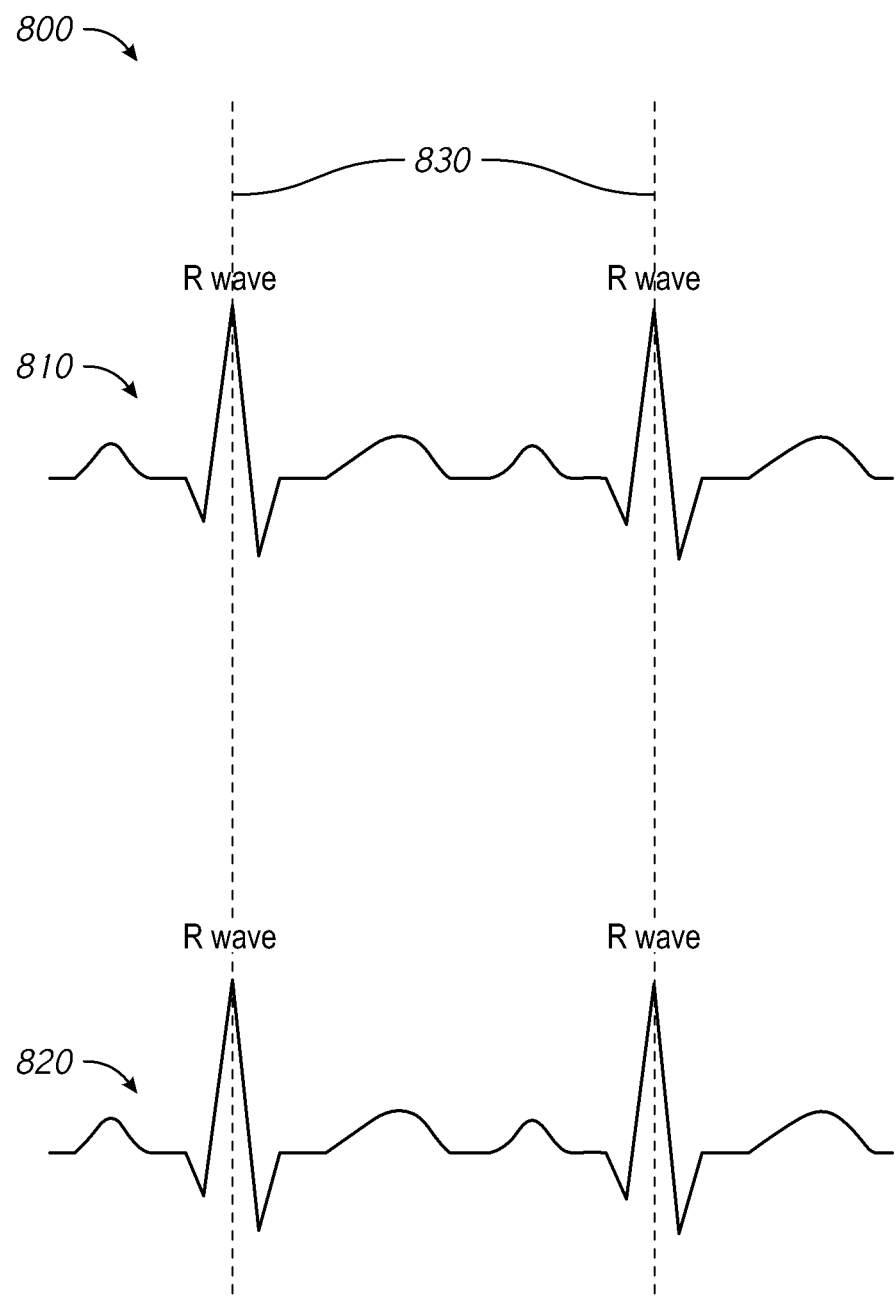
FIG. 14 illustrates electrocardiograms received from two different mapping devices of a system, according to one embodiment.

As represented graphically in FIG. 14 and discussed in greater detail herein, the processor (e.g., processor 650) of an enhanced mapping system (e.g., one that uses two different mapping devices or systems) may need to align or otherwise manipulate the data obtained by each of the mapping systems operatively coupled to the system. For example, in some embodiments, the data are aligned or synchronized by applying an adjustment associated with the R-waves of the various electrocardiograms 810, 820 generated by each of the mapping devices or systems. Alternatively, other cardiac fiducial points may be used, including those coming for other sensor types, such as cardiac pressure sensors. As illustrated in FIG. 14, for example, the - waves can be aligned (e.g., graphically represented by dashed lines 830) in the corresponding electrocardiograms 810, 820 in order for the data obtained by the two devices or systems to be adjusted, and for a corresponding 3D map that integrates the data to be accurate.

According to some embodiments, as and/or after an enhanced 3D map of the targeted anatomical region is obtained, the first device or system (e.g., the catheter with the high-resolution-tip electrode or another type of electrode or energy delivery member) can be used to selectively ablate certain portions of the tissue. For example, as discussed in greater detail herein with reference to FIGS. 15A and 15B, a roving catheter-based system can be used to accurately detect any rotors (e.g., that may be the result of atrial fibrillation or of other cardiac condition) or other features or conditions within a targeted region (e.g., atrium) of a subject and ablate one or more portions of the said region (e.g., to interrupt the rotors). In some embodiments, the first device or system can be used to confirm lesion maturation.

Figure 15A:
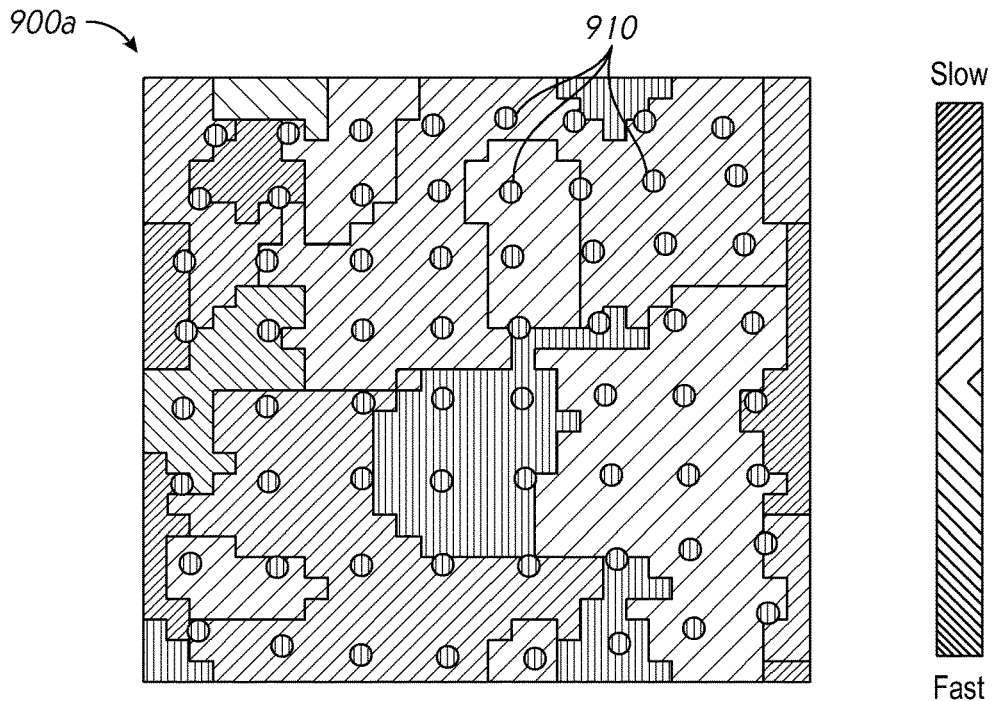
FIG. 15A illustrates one embodiment of a 3D tissue map obtained using only a multi-electrode mapping system.

FIG. 15A illustrates one embodiment of a 3D tissue map 900a obtained using only a multi-electrode system. In the illustrated arrangement, the multi-electrode device or system comprises a total of 64 electrodes that, when expanded within a targeted anatomical structure of a subject (e.g., an atrium), are configured to contact, and thus obtain mapping data, along specific locations of such a targeted anatomical structure. However, in other embodiments, a multi-electrode device or system can include fewer or greater than 64 electrodes, as desired or required. As shown, the 3D rotor map is created using activation timing data (e.g., as illustrated in FIG. 15A). Other types of cardiac maps can be created as well, such as: cardiac activation maps, propagation velocity maps, voltage maps, etc.

As illustrated in the example 3D activation map of FIG. 15A, there exist relatively large gaps or spaces between adjacent electrodes of the multi-electrode device or system. As a result, the corresponding 3D map that is generated using only the multi-electrode mapping device or system may be inaccurate and/or incomplete. For example, in some embodiments, there may exist a rotor or other indicia of a cardiac arrhythmia (e.g., atrial fibrillation) or other condition that may not be identified by the fixed-space electrodes of a multi-electrode mapping device or system.

Figure 15B:
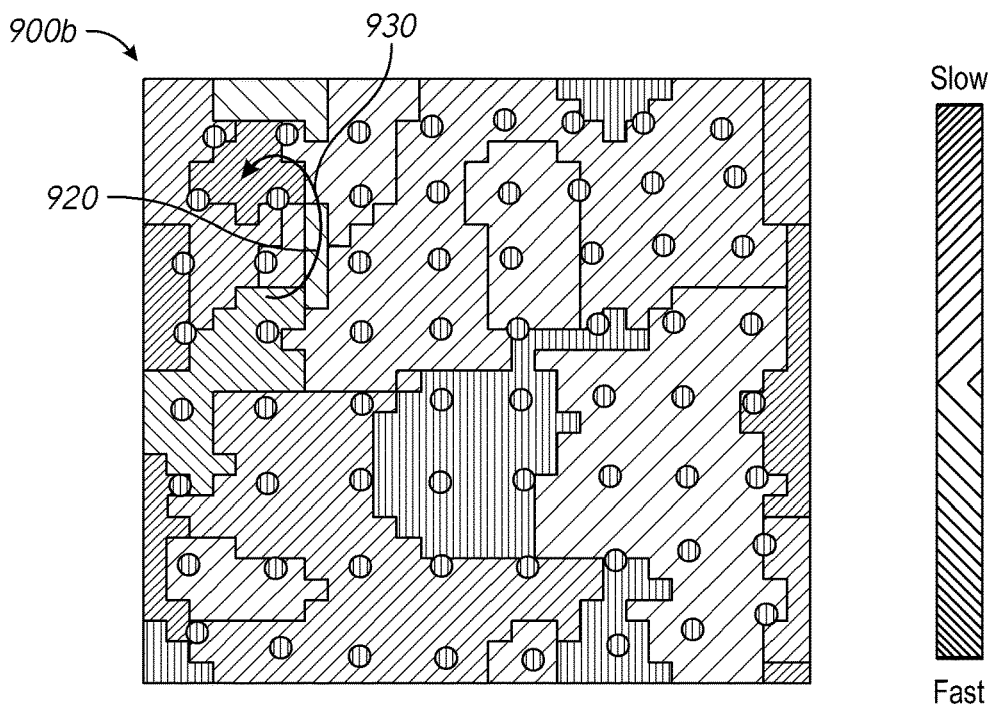
FIG. 15B illustrates the 3D tissue map of FIG. 15A that has been enhanced by high-resolution data obtained using a second mapping device, according to one embodiment.

By way of example, FIG. 15B illustrates a region 920 of the subject's anatomical space that has been mapped using a roving (e.g., catheter-based) device or system, in accordance with the various embodiments disclosed herein. Thus, when contrasted to the 3D map of FIG. 15A, the map of FIG. 15B provides additional mapping data between the set, fixed locations of the electrodes in a multi-electrode device or system. For example, such additional information can be obtained in a region 920 located generally between the various set point locations of the fixed electrodes 910 of the multi-electrode device or system. In some embodiments, such intermediate mapping data can detect a different representation of the status of the corresponding tissue. For example, whereas in FIG. 15A, the tissue located at location 920 is not capable of being specifically mapped, a catheter having a high-resolution-tip electrode (or some other embodiment of a roving mapping electrode) may be able to obtain specific data regarding that intermediate location 920. As a result, an intermediate region (e.g., having a relatively early activation) can be contrasted to data that was obtained by only using the multi-electrode device or system (as shown in FIG. 15A). Consequently, the enhanced mapping system could be used to detect the presence of a rotor 930 (e.g., wherein a region of the targeted anatomical region exhibits a localized area in which activation of said tissue forms a circular or repetitive pattern). Thus, the presence of a condition can be accurately identified, and subsequently treated, using embodiments of the enhanced mapping devices or systems disclosed herein. As enumerated above, the embodiments disclosed herein can be used to generate many types of enhanced cardiac maps, such as, without limitation: cardiac activation maps, cardiac activity propagation velocity maps, cardiac voltage maps and rotor maps. In accordance with several embodiments, the enhanced mapping system facilitates more focused, localized or concentrated ablation targets and/or may reduce the number of ablations required to treat various conditions.

FIG. 16 schematically illustrates a different embodiment 1000 a filtering element 1004 configured for use with any of the mapping devices and systems disclosed herein (e.g., a roving catheter system comprising a high-resolution tip). The schematically depicted arrangement comprises a filter circuit 1004 that permits for the simultaneous application of RF energy (e.g., during the application of energy to targeted tissue to heat or otherwise ablate such tissue) and measurement of EGM recordings (e.g., for high-resolution mapping). Thus, in some embodiments, a capacitor that is placed across two electrodes or electrode portions can be replaced by a filter circuit such as the one schematically depicted in FIG. 16. Any other type of filtering element that permits an electrode to deliver energy (e.g., RF energy) and to obtain high-resolution mapping data can be included in any of the embodiments disclosed herein or variations thereof.

With continued reference to FIG. 16, the filtering element 1004 can include a LC circuit. In some embodiments, such a LC circuit can be tuned and otherwise configured to resonate near the RF energy frequency (e.g. 460 kHz, 400-500 kHz, 440-480 kHz, frequencies between the foregoing values, etc.), such that the electrodes or electrode portions of a high-resolution catheter or other medical instrument or device 20 have a relatively low impedance between them at the RF energy frequency. The impedance of the filter circuit increases dramatically at lower frequencies, such as the frequencies utilized for EGM recordings, thus allowing for the two electrodes to be disconnected from each other to allow an EGM signal to formulate across them. As shown in the arrangement of FIG. 16, the filtering element 1004 can include an EGM recorder 1010 that is operatively coupled to a filter 1012. In addition, the RF generator or other energy delivery module, RF can be operatively coupled to a RF return pad or similar member 1050.

According to some embodiments, in order to achieve a circuit that resonates near a targeted frequency (e.g., 460 kHz) and that provides a high impedance at EGM frequencies, inductor values of 0.7 uH to 1000 uH may be used. In some embodiments, the value of the capacitance can be 0.12 to 170 nF. In some configurations, the LC circuit of such a filtering element 1004 is tuned to resonate at approximately 460 kHz (e.g. 460 kHz, 400-500 kHz, 440-480 kHz, frequencies between the foregoing values, etc.) by maintaining the relationship between L and C values in accordance with eh following formula:

$$C = \frac{1}{L \cdot (2 \cdot \pi \cdot f)^2}$$

Figure 17:
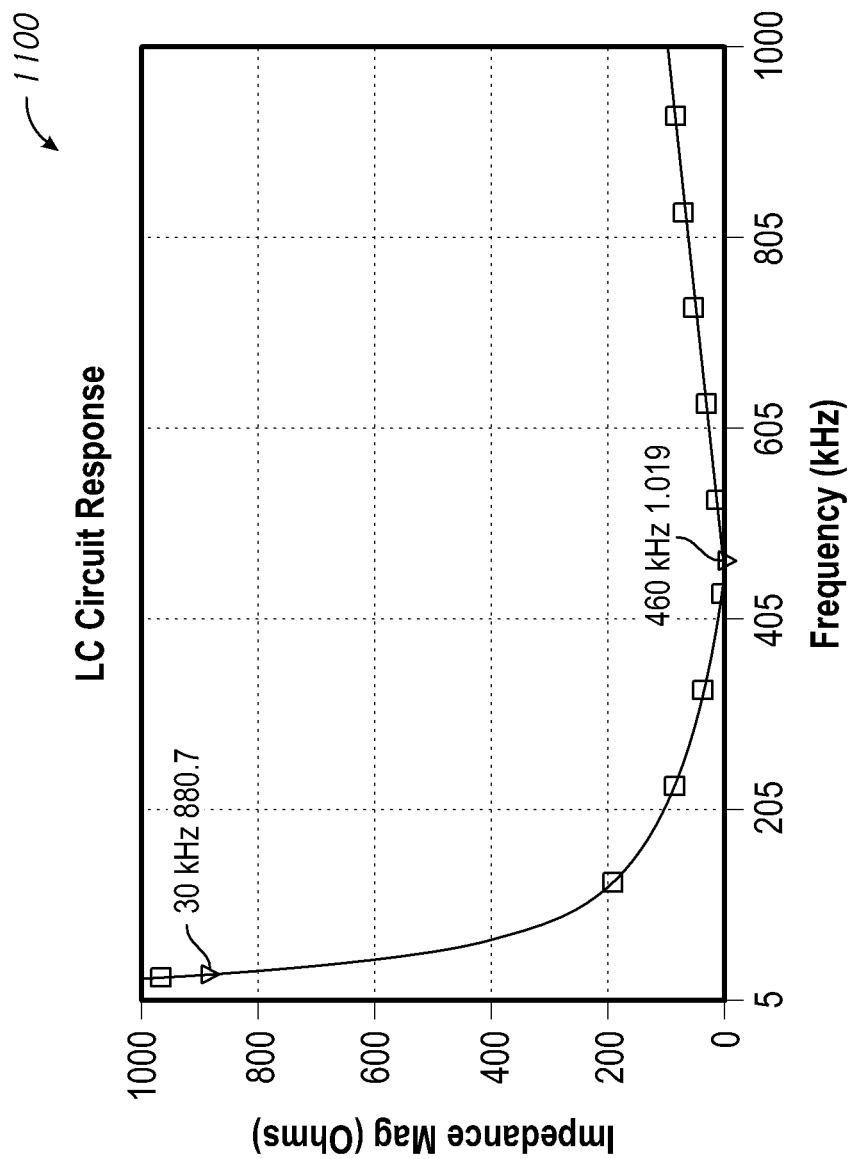
FIG. 17 illustrates one embodiment of a chart depicting impedance magnitude at different frequencies for the filtering element of FIG. 16.

In the formula provided above, C is the capacitance, L is the inductance, and f is the frequency. According to some embodiments, a nominal value for the LC circuit may be L=20 uH and C=6 nF. However, in other configurations, such values can vary, as desired or required for a particular application or design. One embodiment 1100 of impedance magnitude versus frequency response of such LC circuits is graphically illustrated in FIG. 17. As noted herein, such a LC circuit or alternative filtering element can be used in any of the high-resolution embodiments disclosed herein (e.g., in lieu of a capacitor or altering filtering element that permits for both the delivery of energy and the ability to perform high-resolution mapping).

According to some embodiments, due to the nature of the high-resolution-tip electrode systems that are used to create a more complete and comprehensive map of targeted tissue, in accordance with the various high-resolution-tip systems and devices disclosed herein, additional information regarding the position of the roving catheter (and thus, the intermediate mapping locations) can be obtained and provided to the user during a procedure. For example, given the high-resolution mapping capabilities of such catheters, information can be obtained regarding the nature, type and other details regarding the tissue that is adjacent the electrode. In addition, as noted above, the high-resolution-tip embodiments disclosed herein can help determine whether a specific tissue region has been adequately ablated (e.g., see the disclosure above with reference to FIG. 8).

In some embodiments, any of the high-resolution-tip electrode devices or systems disclosed herein can be used as stand-alone mapping systems to accurately assess the condition of a subject's targeted anatomical region, even with the use of a separate mapping system (e.g., such as the one schematically illustrated in FIG. 9). For example, a user can move a high-resolution-tip electrode catheter or other medical instrument to various locations within a subject's anatomy to generate a detailed, accurate and complete electrical map, as desired or required.

As a result of the high-resolution mapping capabilities of the various high-resolution-tip electrode catheter devices and systems disclosed herein, an accurate map of the subject's targeted anatomical space or other region can be obtained. In addition, in view of the fact that such systems are also configured to advantageously ablate tissue, a more efficient and accurate treatment procedure can be attained. For example, in embodiments where one of the high-resolution-tip electrodes devices or systems disclosed herein is being use to map a subject's anatomy (e.g., atrium), either with or without the use of a separate (e.g., commercially-available mapping system), such a high-resolution-tip device or system can be used to also ablate tissue. This can facilitate and improve the execution of a treatment procedure. For example, the ability to use a single device to both map and ablate tissue permits a user to more expeditiously perform an overall assessment and treatment of a subject. In addition, the ability to create a more comprehensive map of the subject's tissue, allows a user to perform a subject treatment procedure with greater accuracy and precision. As discussed, this can help reduce the overall (and sometimes unnecessary) trauma to the subject, improve recovery and provide for better and effective treatment of the subject's disease. In addition, as noted above, the ability of the user to determine whether tissue has already been ablated or otherwise treated to a sufficient level can further improve the efficacy, efficiency and/or safety of a procedure.

In some embodiments, the system comprises various features that are present as single features (as opposed to multiple features). For example, in one embodiment, the system includes a single roving catheter that is configured to obtain high-resolution mapping of tissue and a single separate mapping device or system that includes mapping electrodes for mapping tissue of the subject. The separate mapping device or system can include an at least one expandable member, wherein at least some of the plurality of mapping electrodes of the separate mapping device or system are positioned along the expandable member. The roving catheter is configured to obtain mapping data in tissue regions not adequately covered by the separate mapping device or system. The system can include a single data acquisition device for receiving mapping data from the roving catheter and/or the separate mapping device or system. The system can further include a single processor that is configured to generate a three-dimensional map using the mapping data received by the data acquisition device. Thus, in some embodiments, the system does not require separate processors to receive and process mapping data that are received from separate mapping devices or systems (e.g., a multi-electrode mapping system or device, a roving catheter having a high-resolution electrode, etc.). The roving catheter can include a split-tip electrode design and/or any other high-resolution configuration. The processor can be configured to selectively ablate tissue based on the mapping data obtained from the roving catheter and the separate mapping device or system.

According to some embodiments, the system consists essentially of a roving catheter that is configured to obtain high-resolution mapping of tissue, a separate mapping device or system that includes mapping electrodes for mapping tissue of the subject and a data acquisition device for receiving mapping data from the roving catheter and/or the separate mapping device or system. In some embodiments, the system consists essentially of roving catheter that is configured to obtain high-resolution mapping of tissue, a separate mapping device or system that includes mapping electrodes for mapping tissue of the subject, a data acquisition device for receiving mapping data from the roving catheter and/or the separate mapping device or system and a processor that is configured to generate a three-dimensional map using the mapping data received by the data acquisition device.

In some embodiments, the system comprises various features that are present as single features (as opposed to multiple features). For example, in one embodiment, the system includes a single ablation catheter with a single energy delivery radiofrequency electrode and one or more temperature sensors (e.g., thermocouples) to help determine the temperature of tissue at a depth. The system may comprise an impedance transformation network. Multiple features or components are provided in alternate embodiments.

In some embodiments, the system comprises one or more of the following: means for tissue modulation (e.g., an ablation or other type of modulation catheter or delivery device), means for generating energy (e.g., a generator or other energy delivery module), means for connecting the means for generating energy to the means for tissue modulation (e.g., an interface or input/output connector or other coupling member), means for obtaining mapping data using a multi-electrode mapping system (e.g., an expandable system that engages various portions of targeted tissue), means for obtaining mapping data (e.g., high-resolution data) in areas of the tissue located between the electrodes of a multi-electrode mapping system, means for acquiring data (e.g., using one or more data acquisition devices) from the multi-electrode mapping device or system and/or a device comprising a high-resolution electrode assembly (e.g., a roving catheter), means for processing mapping data obtained from the means for acquiring data (e.g., using a processor) to, e.g., generate a three-dimensional map, etc.

Any methods described herein may be embodied in, and partially or fully automated via, software code modules executed by one or more processors or other computing devices. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

In addition, embodiments may be implemented as computer-executable instructions stored in one or more tangible computer storage media. As will be appreciated by a person of ordinary skill in the art, such computer-executable instructions stored in tangible computer storage media define specific functions to be performed by computer hardware such as computer processors. In general, in such an implementation, the computer-executable instructions are loaded into memory accessible by at least one computer processor. The at least one computer processor then executes the instructions, causing computer hardware to perform the specific functions defined by the computer-executable instructions. As will be appreciated by a person of ordinary skill in the art, computer execution of computer-executable instructions is equivalent to the performance of the same functions by electronic hardware that includes hardware circuits that are hardwired to perform the specific functions. As such, while embodiments illustrated herein are typically implemented as some combination of computer hardware and computer-executable instructions, the embodiments illustrated herein could also be implemented as one or more electronic circuits hardwired to perform the specific functions illustrated herein.

The various systems, devices and/or related methods disclosed herein can be used to at least partially ablate and/or otherwise ablate, heat or otherwise thermally treat one or more portions of a subject's anatomy, including without limitation, cardiac tissue (e.g., myocardium, atrial tissue, ventricular tissue, valves, etc.), a bodily lumen (e.g., vein, artery, airway, esophagus or other digestive tract lumen, urethra and/or other urinary tract vessels or lumens, other lumens, etc.), sphincters, other organs, tumors and/or other growths, nerve tissue and/or any other portion of the anatomy. The selective ablation and/or other heating of such anatomical locations can be used to treat one or more diseases or conditions, including, for example, atrial fibrillation, mitral valve regurgitation, other cardiac diseases, asthma, chronic obstructive pulmonary disease (COPD), other pulmonary or respiratory diseases, including benign or cancerous lung nodules, hypertension, heart failure, denervation, renal failure, obesity, diabetes, gastroesophageal reflux disease (GERD), other gastroenterological disorders, other nerve-related disease, tumors or other growths, pain and/or any other disease, condition or ailment.

In any of the embodiments disclosed herein, one or more components, including a processor, computer-readable medium or other memory, controllers (for example, dials, switches, knobs, etc.), displays (for example, temperature displays, timers, etc.) and/or the like are incorporated into and/or coupled with (for example, reversibly or irreversibly) one or more modules of the generator, the irrigation system (for example, irrigant pump, reservoir, etc.) and/or any other portion of an ablation or other modulation system.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter" or "delivering energy to an ablation member" include "instructing advancing a catheter" or "instructing delivering energy to an ablation member," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A system for obtaining mapping data for a targeted anatomical tissue of a subject, the system comprising:
   a catheter comprising at least electrode configured to map tissue along the targeted anatomical tissue; and
   a data acquisition device configured to receive mapping data from the catheter;
   the data acquisition device is configured to couple to a separate mapping device, the data acquisition device being configured to receive mapping data from the separate mapping device, wherein the separate mapping device comprises a plurality of mapping electrodes, the plurality of mapping electrodes including at least a first electrode member and a second electrode member coupled with a filtering element, the filtering element being configured to:
   allow the simultaneous application of radiofrequency ablation energy from the first electrode member and the second electrode member at a first radiofrequency range; and
   allow the first electrode member and the second electrode member to operate as separate electrodes to facilitate mapping at a second frequency range different than the first frequency range; and
   a processor configured to generate a three-dimensional map from the mapping data received from the catheter and the separate mapping device by the data acquisition device.

2. The system of claim 1, wherein the separate mapping device comprises at least one expandable member, wherein at least some of the plurality of mapping electrodes are positioned along the at least one expandable member.

3. The system of claim 1, wherein the mapping data received from the separate mapping device comprise unipolar or bipolar signals.

4. The system of claim 1, wherein the processor is configured to or synchronize mapping data obtained from the catheter and the separate mapping device.

5. The system of claim 1, wherein the processor is configured to couple to an output device for displaying the three-dimensional map.

6. The system of claim 1, wherein the processor is integrated within the data acquisition device.

7. The system of claim 1, wherein the processor is separate from the data acquisition device.

8. A system for obtaining mapping data for a targeted anatomical tissue of a subject, the system comprising:
- a data acquisition device configured to receive mapping data from a mapping catheter; and
- a processor configured to receive mapping data from the data acquisition device and from a separate mapping system, wherein the separate mapping system is configured to operatively couple to the processor, the separate mapping system comprising a plurality of mapping electrodes, the plurality of mapping electrodes including at least a first electrode member and a second electrode member coupled with a filtering element, the filtering element being configured to:
- allow the simultaneous application of radiofrequency ablation energy from the first electrode member and the second electrode member at a first radiofrequency range; and
- allow the first electrode member and the second electrode member to operate as separate electrodes to facilitate mapping at a second frequency range different than the first frequency range; and the processor is configured to generate a three-dimensional map from such mapping data.

9. The system of claim 8, wherein the system is configured to operatively couple to an output device for displaying said three-dimensional map.

10. The system of claim 8, wherein the mapping catheter includes a tip tip electrode.

11. The system of claim 8, wherein the separate mapping system comprises at least one expandable member, the at least one expandable member comprising at least one of the plurality of mapping electrodes.

12. The system of claim 11, wherein the separate mapping system comprises an expandable basket.

13. The system of claim 8, wherein the processor is configured to align or synchronize data obtained from the mapping catheter and from the separate mapping system.

14. The system of claim 8, wherein the processor is separate from the data acquisition device.

* * * * *